(12) United States Patent
Uhlmann et al.

(10) Patent No.: US 8,772,469 B2
(45) Date of Patent: Jul. 8, 2014

(54) SYNTHETIC DOUBLE-STRANDED OLIGONUCLEOTIDES FOR SPECIFIC INHIBITION OF GENE EXPRESSION

(75) Inventors: Eugen Uhlmann, Glashütten (DE); Jochen Huber, Maxdorf (DE); Niki Gunkel, Heidelberg (DE); Sandra Neumann, Offenbach (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/193,747

(22) Filed: Jul. 11, 2002

(65) Prior Publication Data

US 2003/0139585 A1    Jul. 24, 2003

(30) Foreign Application Priority Data

Jul. 12, 2001   (DE) .................................. 101 33 858

(51) Int. Cl.
   *C07H 21/02*   (2006.01)
(52) U.S. Cl.
   USPC ........................................................ 536/24.5
(58) Field of Classification Search
   USPC ................. 536/23.1, 24.2, 24.3, 24.5; 514/44
   See application file for complete search history.

(56) References Cited

U.S. PATENT DOCUMENTS

| | | | |
|---|---|---|---|
| 5,532,130 A | | 7/1996 | Alul |
| 5,583,032 A | * | 12/1996 | Torrence et al. ............. 435/91.1 |
| 5,817,796 A | * | 10/1998 | Stinchcomb et al. ........ 536/24.5 |
| 5,886,165 A | | 3/1999 | Kandimalla et al. ......... 536/23.1 |
| 6,033,909 A | | 3/2000 | Uhlmann et al. |
| 6,316,194 B1 | * | 11/2001 | Karn et al. .................... 435/6.18 |
| 6,670,461 B1 | * | 12/2003 | Wengel et al. ................ 536/23.1 |
| 2004/0259247 A1 | * | 12/2004 | Tuschl et al. .................. 435/375 |

FOREIGN PATENT DOCUMENTS

| | | |
|---|---|---|
| WO | WO 89/03683 | 5/1989 |
| WO | WO 94/01550 | * 1/1994 |
| WO | WO 99/58702 | 11/1999 |
| WO | WO 99/58723 | 11/1999 |
| WO | WO 00/04189 | 1/2000 |
| WO | WO 00/49035 | 8/2000 |

OTHER PUBLICATIONS

Burlina et al. Clevage activity of a hammerhead ribozyme domain containing 2',5'-phosphodiester linkages. Jun. 1999. Tetrahedron Letters vol. 40, pp. 4559-4562.*
Damha et al. (1998) Nucleic Acids Res. 26:5152-5156.*
Giannaris et al. (1993) Nucleic Acids Res. 21:4742-4749.*
Xiao et al. (1998) J. Med. Chem. 41:1531-1539.*
Jen et al. (2000) Stem Cells 18:307-319.*
Opalinska et al. (2002) Nature Reviews 1 :503-514.*
Prakash et al. (2006) Bioorganic & Medicinal Chemistry Letters. 16:3238-3240.*
Kandimallah et al (Nucl. Acids Res. 25(2): 370-378, 1997).*
Paddison et al (Genes Dev. 16:948-958, Apr. 15, 2002).*
Torrence et al (Proc. Nat. Acad. Sci. USA 901:1300-1304, 1993).*
Bass Brenda L, The Short Answer, Nature, vol. 411, May 24, 2001, pp. 428-429.
Doetsch Paul et al., Synthesis and Characterization of (2'-5')ppp3'da(p3'da) An Analogue of (2'-5')ppA(pA), Nature (1981) 291 pp. 355-358.
Elbashir Sayda M et al., Duplexes of 21-nucleotide RNAs Mediate RNA Interference in Cultured Mammalian Cells, Nature, vol. 411, May 24, 2001, pp. 494-498.
Engels J W et al., Chemistry of Oligonucleotides, Taylor & Francis, London (2000): pp. 35-78.
Froehler Brian C et al., Triple-Helix Formation by Oligodeoxynucleotides Containing the Carbocyclic Analogs of Thymidine and 5-Methyl-2'-deoxycytidine, Journal of American Chemical Society, 1992, 114, pp. 8320-8322.
Hayashi S-I et al., In Vivo Transfer of Gene and Oligodeoxynucleotides into Skin of Fetal Rats by Incubation in Amniotic Fluid, Gene Therapy, vol. 3, 1996, pp. 878-885.
Herdewijn P, Conformationally Restricted Carbohydrate-modified Nucleic Acids and Antisense Technology, Biochimica et Biophysica Acta 1489 (1999); pp. 167-179.
Herdewijn Piet, Heterocyclic Modifications of Oligonucleotides and Antisense Technology, Antisense & Nucleic Acid Drug Development 10:297-310 (2000).
Iyer Radhakrishnan P et al., Modified Oligonucleotides—Synthesis, Properties and Applications, Current Opinion in Molecular Therapeutics (1999) 1(3):344-358.
Koga Masakazu et al., Alternating a,B-Oligothymidylates with Alternating (3'→3')- and (5'→5')-Internucleotidic Phosphodiester Linkages as Models for Antisense Oligodeoxyribonucleotides, The Journal of Organic Chemistry. vol. 56, No. 12, Jun. 7, 1991, pp. 3757-3759.
MA Michael Y.X. et al., Design and Synthesis of RNA Miniduplexes Via a Synthetic Linker Approach, Biochemistry, American Chemical Society (1993) 32 pp. 1751-1758.
Manoharan Muthiah, 2'-Carbohydrate Modifications in Antisense Oligonucleotide Therapy: Importance of Conformation, Configuration and Conjugation, Biochimica et Biophysics Acta 1489 (1989), pp. 117-130.
Nielsen Peter E et al., Peptide Nucleic Acid (PNA). A DNA Mimic with a Peptide Backbone, Bioconjugate Chem. 1994, 5, pp. 3-7.
Player Mark R et al., The 2-5A System: Modulation of Viral and Cellular Processes Through Acceleration of RNA Degradation, Pharmacol. Ther., vol. 78, No. 2, 1998, pp. 55-113.
Singh Sanjay K et al., LNA (Locked Nucleic Acids): Synthesis and High-affinity Nucleic Acid Recognition, Chem. Commun., 1998, pp. 455-456.
Singh Sanjay K et al., Universality of LNA-mediated High-affinity Nucleic Acid Recognition, Chem. Commun., 1998, pp. 1247-1248.
Stirchak Eugene P et al., Uncharged Stereoregular Nucleic Acid Analogs: 2. Morpholino Nucleoside Oligomers with Carbamate Internucleoside Linkages, Nucleic Acids Research, vol. 17, No. 15, 1989, pp. 6129-6141.

(Continued)

*Primary Examiner* — Richard Schnizer
(74) *Attorney, Agent, or Firm* — Lathrop & Gage LLP; James H. Velema, Esq.

(57) ABSTRACT

The present invention relates to oligonucleotide derivatives which are at least partly double-stranded and which have a 2'5'-linked oligonucleotide residue on at least one 3' end and to the use thereof for specific inhibition of gene expression.

25 Claims, No Drawings

(56) References Cited

OTHER PUBLICATIONS

Summerton James et al., Morpholino Antisense Oligomers: Design, Preparation, and Properties, Antisense & Nucleic Acid Drug Development, vol. 7 (1997), pp. 187-195.

Tarkoy Markus et al., Nucleic-Acid Analogues with Constraint Conformational Flexibility in the Sugar-Phosphate Backbone ('Bicyclo-DNA'), Helvetica Chimica Acta, vol. 76, 1993, pp. 481-510.

Torrence P F et al., Development of 2',5'-0ligonucleotides as Potential Therapeutic Agents, Current Medicinal Chemistry, 1994, 1, 176-191.

Torrence Paul F et al., Targeting RNA for Degradation with a (2'-5') Oligoadenylate-antisense Chimera, Proc. Natl. Acad. Sci., USA, vol. 90, Feb. 1993, pp. 1300-1304.

Uhlmann Eugen et al., Antisense Oligonucleotides: A New Therapeutic Principle, Chemical Reviews, vol. 90, No. 4, Jun. 1990.

Uhlmann Eugen et al., Oligonucleotide Analogs Containing Dephospho-lnternucleoside Linkages, Methods in Molecular Biology, vol. 20, 1993, pp. 355-389.

Uhlmann Eugen et al., Synthesis and Properties of PNA/DNA Chimeras, Angew. Chem. Int. Ed. Engl. 1996, 35, No. 22, pp. 2632-2638.

Uhlmann Eugen, Recent Advances in the Medicinal Chemistry of Antisense Oligonucleotides, Current Opinion in Drug Discovery & Development 2000 3(2):203-213.

Vandendriessche Frank et al., Acyclic Oligonudeotides: Possibilities and Limitations, Tetrahedron vol. 49, No. 33, 1993, pp. 7223-7238.

Verma Sandeep et al., Modified Oligonucleotides: Synthesis and Strategy for Users, Annu. Rev. Biochem. 1998, 67:99-134.

Weiner Norman et al., Liposomes as a Drug Delivery System, Drug Development and Industrial Pharmacy, 15 (10); 1989, pp. 1523-1554.

Woolf Tod M et al., Specificity of Antisense Oligonucleotides in Vivo, Proc. Natl. Acad. Sci., USA, vol. 89, Aug. 1992, pp. 7305-7309.

Herdewijn Piet, Heterocyclic Modifications of Oligonucleotides and Antisense Technology, Antisense & Nucleic Acid Drug Development vol. 10 (2000), pp. 297-310.

Iyer Radhakrishnan P. et al., Modified Oligonucleotides—Synthesis, Properties and Applications, Current Opinion in Molecular Therapeutics, vol. 1(3), 1999 pp. 344-358.

Koga Masakazu et al., Alternating a,B-Oligothymidylates with Alternating (3'→3')- and (5'→5')-Internucleotidic Phosphodiester Linkages as Models for Antisense Oligodeoxyribonucleotides, The Journal of Organic Chemistry. vol. 56, No. 12, Jun. 7, 1991, pp. 3757-3759.

Manoharan Muthiah, 2'-Carbohydrate Modifications in Antisense Oligonucleotide Therapy: Importance of Conformation, Configuration and Conjugation, Biochimica et Biophysics Acta 1489 (1989), pp. 117-130.

Singh Sanjay K et al., LNA (Locked Nucleic Adds): Synthesis and High-affinity Nucleic Acid Recognition, Chem. Commun., 1998, pp. 455-456.

Torrence P F et al., Development of 2',5'-Oligonucleotides as Potential Therapeutic Agents, Current Medicinal Chemistry, 1994, 1, pp. 176-191.

Uhlmann Eugen et al., Antisense Oligonucleotides: A New Therapeutic Principle, Chemical Reviews, vol. 90, No. 4, Jun. 1990, pp. 543.

Uhlmann Eugen et al., Oligonucleotide Analogs Containing Dephospho-internucleoside Linkages, Methods in Molecular Biology, vol. 20, 1993, pp. 355-389.

Uhlmann Eugen et al., Synthesis and Properties of PNA/DNA Chimeras, Angew. Chem. Int. Ed. Engl. 1996. 35, No. 22, pp. 2632-2638.

Uhlmann Eugen, Recent Advances in the Medicinal Chemistry of Antisense Oligonucleotides, Current Opinion in Drug Discovery & Development 2000, vol. 3(2), pp. 203-213.

Vandendriessche Frank et al., Acyclic Oligonucleotides: Possibilities and Limitations, Tetrahedron vol. 49, No. 33, 1993, pp. 7223-7238.

Verma Sandeep et al., Modified Oligonucleotides: Synthesis and Strategy for Users, Annu. Rev. Biochem. 1998, vol. 67, pp. 99-134.

Jaffe et al., Culture of Human Endothelial Cells Derived from Umbilical Veins, The Journal of Clinical Investigation vol. 52, Nov. 1973, pp. 2745-2756.

Torrence et al., Targeting RNA for Degradation . . . Chimera. PNAS 90, 1300-1304, 1993.

Elbashir et al., RNA interference is mediated by 21- and 22-nucleotide RNAs, Genes & Dev., 2001, vol. 15, pp. 188-200.

Li et al., Synthesis and Properties of Second-Generation 2-5A-Antisense Chimeras with Enhanced Resistance to Exonucleases, J. Med. Chem., 1997, vol. 40, pp. 2959-2966.

Verheijen et al., Incorporation of a 4-Hydroxy-N-acetylprolinol Nucleotide Analogue Improves the 30-Exonuclease Stability of 2'-5'-Oligoadenylate-Antisense Conjugates, Biorg. & Med. Chem. Letters, vol. 10, 2000, pp. 801-804.

Agrawal et al., Antisense therapeutics: is it as simple as complementary base recognition?, Molecular Medicine Today, vol. 6, Feb. 2000, pp. 72-81.

Branch, A., A good antisense molecule is hard to find, Trends in Biochem. Sci., vol. 23, 1998: pp. 45-50.

Chirila et al., The use of synthetic polymers for delivery of therapeutic antisense oligodeoxynucleotides, Biomaterials, vol. 23, 2002, pp. 321-342.

Crooke, S.T., Progress in Antisense Techology, Annu. Rev. Med. vol. 55, 2004, pp. 61-95.

Kandimalla et al., Mixed backbone antisense oligonucleotides: design, biochemical and biological properties of oligonucleotides containing 2'-5'-ribo-and 3'-5'-deoxyribonucleotide segments, Nucleic Acids Research, vol. 25, No. 2, 1997, pp. 370-378.

Leaman et al., Controlling Gene Expression with 2-5A Antisense, Methods: A Comparison to Methods in Enzymology, vol. 18, 1999, pp. 252-265.

Peracchi, A., Prospects for antiviral ribozymes and dexoyribozymes, Rev. Med. Virol. vol. 14. 2004, pp. 47-64.

Torrence et al., Oligonucleotide Structural Parameters That Influence Binding of 5'-O-Triphosphoadenylyl-(2'-5')-adenylyl-(2'-5')-adenosin to the 5'-O-Triphosphoadenylyl-(2'-5') . . . , J. Med. Chem. vol. 27, 1984, pp. 726-733.

Chakrabarti, et al: New Insights into the Role of RNase L in Innate Immunity; J. Interferon & Cytokine Res.; 2011, vol. 31, No. 1, pp. 49-57.

Maitra, et al: Catalytic Cleavage of an RNA Target by 2-5A Antisense and RNase L; J. Biol. Chem.; 1995, vol. 270, No. 25, pp. 15071-15075.

Silverman, et al: Viral Encounters with 2',5'-Oligoadenylate Synthetase and RNase L during the Interferon Antiviral Response; 2007, vol. 81, No. 23, pp. 12720-12729.

Xiao, et al: Nuclease-Resistant Composite 2',5'-Oligoadenylate-3',5'-Oligonucleotides for the Targeted Destruction of RNA: 2-5A-Iso-antisense; J. Med. Chem.; 1998, No. 41, pp. 1531-1539.

Zhou, et al: Endowing RNase H-Inactive Antisense with Catalytic Activity: 2-5A-Morphants; Bioconjugate Chem.; 2005, No. 16, pp. 383-390.

* cited by examiner

SEQUENCE LISTING

<160> NUMBER OF SEQ ID NOS: 40

<210> SEQ ID NO 1
<211> LENGTH: 25
<212> TYPE: DNA
<213> ORGANISM: Artificial
<220> FEATURE:
<221> NAME/KEY: misc_feature
<223> OTHER INFORMATION: Part of Photinus pyralis Luziferase

<400> SEQUENCE: 1
ttttgaagcg aaggttgtgg atctg                                    25

<210> SEQ ID NO 2
<211> LENGTH: 25
<212> TYPE: RNA
<213> ORGANISM: Artificial Sequence
<220> FEATURE:
<223> OTHER INFORMATION: Part of Photinus pyralis Luziferase
<220> FEATURE:
<221> NAME/KEY: misc_feature
<223> OTHER INFORMATION: Part of Photinus pyralis Luziferase

<400> SEQUENCE: 2
uuuugaagcg aagguugugg aucug                                    25

<210> SEQ ID NO 3
<211> LENGTH: 80
<212> TYPE: DNA
<213> ORGANISM: Artificial Sequence
<220> FEATURE:
<223> OTHER INFORMATION: Part of Photinus pyralis Luziferase
<220> FEATURE:
<221> NAME/KEY: misc_feature
<223> OTHER INFORMATION: Part of Photinus pyralis Luziferase

<400> SEQUENCE: 3
gcttttacag atgcacatat cgaggtggac atcacttacg cgaaaatgtc tacgtgtata    60
gctccacctg tagtgaatgc                                              80

<210> SEQ ID NO 4
<211> LENGTH: 80
<212> TYPE: DNA
<213> ORGANISM: Artificial Sequence
<220> FEATURE:
<223> OTHER INFORMATION: Part of Photinus pyralis Luziferase
<220> FEATURE:
<221> NAME/KEY: misc_feature
<223> OTHER INFORMATION: Part of Photinus pyralis Luziferase

<400> SEQUENCE: 4
ccgcgaacga catttataat gaacgtgaat tgctcaacag ggcgcttgct gtaaatatta    60
cttgcactta acgagttgtc                                              80

<210> SEQ ID NO 5
<211> LENGTH: 80
<212> TYPE: DNA
<213> ORGANISM: Artificial Sequence
<220> FEATURE:
<223> OTHER INFORMATION: Part of Photinus pyralis Luziferase
<220> FEATURE:
<221> NAME/KEY: misc_feature
<223> OTHER INFORMATION: Part of Photinus pyralis Luziferase

<400> SEQUENCE: 5
gcggtcggta aagttgttcc attttttgaa gcgaaggttg cgccagccat ttcaacaagg    60
taaaaaactt cgcttccaac                                                    80

<210> SEQ ID NO 6
<211> LENGTH: 80
<212> TYPE: DNA
<213> ORGANISM: Artificial Sequence
<220> FEATURE:
<223> OTHER INFORMATION: Part of Photinus pyralis Luziferase
<220> FEATURE:
<221> NAME/KEY: misc_feature
<223> OTHER INFORMATION: Part of Photinus pyralis Luziferase

<400> SEQUENCE: 6 atttttttgaa gcgaaggttg tggatctgga taccgggaaa taaaaaactt cgcttccaac       60
acctagacct atggcccttt                                                    80

<210> SEQ ID NO 7
<211> LENGTH: 40
<212> TYPE: RNA
<213> ORGANISM: Artificial Sequence
<220> FEATURE:
<223> OTHER INFORMATION: Part of Photinus pyralis Luziferase
<220> FEATURE:
<221> NAME/KEY: misc_feature
<223> OTHER INFORMATION: Part of Photinus pyralis Luziferase

<400> SEQUENCE: 7
gcuuuuacag augcacauau cgagguggac aucacuuacg                              40

<210> SEQ ID NO 8
<211> LENGTH: 40
<212> TYPE: RNA
<213> ORGANISM: Artificial Sequence
<220> FEATURE:
<223> OTHER INFORMATION: Part of Photinus pyralis Luziferase
<220> FEATURE:
<221> NAME/KEY: misc_feature
<223> OTHER INFORMATION: Part of Photinus pyralis Luziferase

<400> SEQUENCE: 8
cguaagugau guccaccucg auaugugcau cuguaaaagc                              40

<210> SEQ ID NO 9
<211> LENGTH: 40
<212> TYPE: RNA
<213> ORGANISM: Artificial Sequence
<220> FEATURE:
<223> OTHER INFORMATION: Part of Photinus pyralis Luziferase
<220> FEATURE:
<221> NAME/KEY: misc_feature
<223> OTHER INFORMATION: Part of Photinus pyralis Luziferase

<400> SEQUENCE: 9
ccgcgaacga cauuuauaau gaacgugaau ugcucaacag                              40

<210> SEQ ID NO 10
<211> LENGTH: 40
<212> TYPE: RNA
<213> ORGANISM: Artificial Sequence
<220> FEATURE:
<223> OTHER INFORMATION: Part of Photinus pyralis Luziferase
<220> FEATURE:
<221> NAME/KEY: misc_feature
<223> OTHER INFORMATION: Part of Photinus pyralis Luziferase

<400> SEQUENCE: 10
cuguugagca auucacguuc auuauaaaug ucguucgcgg                              40

```
<210> SEQ ID NO 11
<211> LENGTH: 40
<212> TYPE: RNA
<213> ORGANISM: Artificial Sequence
<220> FEATURE:
<223> OTHER INFORMATION: Part of Photinus pyralis Luziferase
<220> FEATURE:
<221> NAME/KEY: misc_feature
<223> OTHER INFORMATION: Part of Photinus pyralis Luziferase

<400> SEQUENCE: 11
gcggucggua aaguuguucc auuuuuugaa gcgaagguug                              40

<210> SEQ ID NO 12
<211> LENGTH: 40
<212> TYPE: RNA
<213> ORGANISM: Artificial Sequence
<220> FEATURE:
<223> OTHER INFORMATION: Part of Photinus pyralis Luziferase
<220> FEATURE:
<221> NAME/KEY: misc_feature
<223> OTHER INFORMATION: Part of Photinus pyralis Luziferase

<400> SEQUENCE: 12
caaccuucgc uucaaaaaau ggaacaacuu uaccgaccgc                              40

<210> SEQ ID NO 13
<211> LENGTH: 40
<212> TYPE: RNA
<213> ORGANISM: Artificial Sequence
<220> FEATURE:
<223> OTHER INFORMATION: Part of Photinus pyralis Luziferase
<220> FEATURE:
<221> NAME/KEY: misc_feature
<223> OTHER INFORMATION: Part of Photinus pyralis Luziferase

<400> SEQUENCE: 13
auuuuuugaa gcgaagguug uggaucugga uaccgggaaa                              40

<210> SEQ ID NO 14
<211> LENGTH: 40
<212> TYPE: RNA
<213> ORGANISM: Artificial Sequence
<220> FEATURE:
<223> OTHER INFORMATION: Part of Photinus pyralis Luziferase
<220> FEATURE:
<221> NAME/KEY: misc_feature
<223> OTHER INFORMATION: Part of Photinus pyralis Luziferase

<400> SEQUENCE: 14
uuucccggua uccagaucca caaccuucgc uucaaaaaau                              40

<210> SEQ ID NO 15
<211> LENGTH: 26
<212> TYPE: RNA
<213> ORGANISM: Artificial Sequence
<220> FEATURE:
<223> OTHER INFORMATION: Part of Photinus pyralis Luziferase
<220> FEATURE:
<221> NAME/KEY: misc_feature
<223> OTHER INFORMATION: Part of Photinus pyralis Luziferase

<400> SEQUENCE: 15
uacagaugca cauaucgagg ugaaaa                                             26

<210> SEQ ID NO 16
<211> LENGTH: 26
<212> TYPE: RNA
```

```
<213> ORGANISM: Artificial Sequence
<220> FEATURE:
<223> OTHER INFORMATION: Part of Photinus pyralis Luziferase
<220> FEATURE:
<221> NAME/KEY: misc_feature
<223> OTHER INFORMATION: Part of Photinus pyralis Luziferase

<400> SEQUENCE: 16
caccucgaua ugugcaucug uaaaaa                                          26

<210> SEQ ID NO 17
<211> LENGTH: 25
<212> TYPE: RNA
<213> ORGANISM: Artificial Sequence
<220> FEATURE:
<223> OTHER INFORMATION: Part of Photinus pyralis Luziferase
<220> FEATURE:
<221> NAME/KEY: misc_feature
<223> OTHER INFORMATION: Part of Photinus pyralis Luziferase

<400> SEQUENCE: 17
uauaaugaac gugaauugcu caaaa                                           25

<210> SEQ ID NO 18
<211> LENGTH: 25
<212> TYPE: RNA
<213> ORGANISM: Artificial Sequence
<220> FEATURE:
<223> OTHER INFORMATION: Part of Photinus pyralis Luziferase
<220> FEATURE:
<221> NAME/KEY: misc_feature
<223> OTHER INFORMATION: Part of Photinus pyralis Luziferase

<400> SEQUENCE: 18
gagcaauuca cguucauuau aaaaa                                           25

<210> SEQ ID NO 19
<211> LENGTH: 25
<212> TYPE: RNA
<213> ORGANISM: Artificial Sequence
<220> FEATURE:
<223> OTHER INFORMATION: Part of Photinus pyralis Luziferase
<220> FEATURE:
<221> NAME/KEY: misc_feature
<223> OTHER INFORMATION: Part of Photinus pyralis Luziferase

<400> SEQUENCE: 19
gguaaaguug uuccauuuuu uaaaa                                           25

<210> SEQ ID NO 20
<211> LENGTH: 25
<212> TYPE: RNA
<213> ORGANISM: Artificial Sequence
<220> FEATURE:
<223> OTHER INFORMATION: Part of Photinus pyralis Luziferase
<220> FEATURE:
<221> NAME/KEY: misc_feature
<223> OTHER INFORMATION: Part of Photinus pyralis Luziferase

<400> SEQUENCE: 20
aaaaaaugga acaacuuuac caaaa                                           25

<210> SEQ ID NO 21
<211> LENGTH: 25
<212> TYPE: RNA
<213> ORGANISM: Artificial Sequence
<220> FEATURE:
<223> OTHER INFORMATION: Part of Photinus pyralis Luziferase
<220> FEATURE:
```

-continued

<221> NAME/KEY: misc_feature
<223> OTHER INFORMATION: Part of Photinus pyralis Luziferase

<400> SEQUENCE: 21
gaagcgaagg uuguggaucu gaaaa                                          25

<210> SEQ ID NO 22
<211> LENGTH: 25
<212> TYPE: RNA
<213> ORGANISM: Artificial Sequence
<220> FEATURE:
<223> OTHER INFORMATION: Part of Photinus pyralis Luziferase
<220> FEATURE:
<221> NAME/KEY: misc_feature
<223> OTHER INFORMATION: Part of Photinus pyralis Luziferase

<400> SEQUENCE: 22
cagauccaca accuucgcuu caaaa                                          25

<210> SEQ ID NO 23
<211> LENGTH: 21
<212> TYPE: RNA
<213> ORGANISM: Artificial Sequence
<220> FEATURE:
<223> OTHER INFORMATION: Part of Photinus pyralis Luziferase
<220> FEATURE:
<221> NAME/KEY: misc_feature
<223> OTHER INFORMATION: Part of Photinus pyralis Luziferase

<400> SEQUENCE: 23
gaagcgaagg uuguggaucu g                                              21

<210> SEQ ID NO 24
<211> LENGTH: 27
<212> TYPE: RNA
<213> ORGANISM: Artificial Sequence
<220> FEATURE:
<223> OTHER INFORMATION: Part of Photinus pyralis Luziferase
<220> FEATURE:
<221> NAME/KEY: misc_feature
<223> OTHER INFORMATION: Part of Photinus pyralis Luziferase

<400> SEQUENCE: 24
cagauccaca accuucgcuu caaaaaa                                        27

<210> SEQ ID NO 25
<211> LENGTH: 60
<212> TYPE: RNA
<213> ORGANISM: Artificial Sequence
<220> FEATURE:
<223> OTHER INFORMATION: Part of human EDG1
<220> FEATURE:
<221> NAME/KEY: misc_feature
<223> OTHER INFORMATION: Part of Human EDG1

<400> SEQUENCE: 25
gaccucggug guguucauuc ucaucugcug cuuuaucauc cuggagaaca ucuuugucuu    60

<210> SEQ ID NO 26
<211> LENGTH: 60
<212> TYPE: RNA
<213> ORGANISM: Artificial Sequence
<220> FEATURE:
<223> OTHER INFORMATION: Part of human EDG1
<220> FEATURE:
<221> NAME/KEY: misc_feature
<223> OTHER INFORMATION: Part of human EDG1

<400> SEQUENCE: 26
aagacaaaga uguucuccag gaugauaaag cagcagauga gaaugaacac caccgagguc    60

<210> SEQ ID NO 27
<211> LENGTH: 60
<212> TYPE: RNA
<213> ORGANISM: Artificial Sequence
<220> FEATURE:
<223> OTHER INFORMATION: Part of human EDG1
<220> FEATURE:
<221> NAME/KEY: misc_feature
<223> OTHER INFORMATION: Part of human EDG1

<400> SEQUENCE: 27
auuuccaagg ccagccgcag cucugagaau guggcgcugc ucaagaccgu aauuaucguc    60

<210> SEQ ID NO 28
<211> LENGTH: 60
<212> TYPE: RNA
<213> ORGANISM: Artificial Sequence
<220> FEATURE:
<223> OTHER INFORMATION: Part of human EDG1
<220> FEATURE:
<221> NAME/KEY: misc_feature
<223> OTHER INFORMATION: Part of human EDG1

<400> SEQUENCE: 28
gacgauaauu acggucuuga gcagcgccac auucucagag cugcggcugg ccuuggaaau    60

<210> SEQ ID NO 29
<211> LENGTH: 21
<212> TYPE: RNA
<213> ORGANISM: Artificial Sequence
<220> FEATURE:
<223> OTHER INFORMATION: Part of human EDG1
<220> FEATURE:
<221> NAME/KEY: misc_feature
<223> OTHER INFORMATION: Part of human EDG1

<400> SEQUENCE: 29
aucauccugg agaacaucuu u                                              21

<210> SEQ ID NO 30
<211> LENGTH: 25
<212> TYPE: RNA
<213> ORGANISM: Artificial Sequence
<220> FEATURE:
<223> OTHER INFORMATION: Part of human EDG1
<220> FEATURE:
<221> NAME/KEY: misc_feature
<223> OTHER INFORMATION: Prat of human EDG1

<400> SEQUENCE: 30
aaagauguuc uccaggauga uaaaa                                          25

<210> SEQ ID NO 31
<211> LENGTH: 21
<212> TYPE: RNA
<213> ORGANISM: Artificial Sequence
<220> FEATURE:
<223> OTHER INFORMATION: Part of human EDG1
<220> FEATURE:
<221> NAME/KEY: misc_feature
<223> OTHER INFORMATION: Part of human EDG1

<400> SEQUENCE: 31
ccaaggccag ccgcagcucu g                                              21

```
<210> SEQ ID NO 32
<211> LENGTH: 25
<212> TYPE: RNA
<213> ORGANISM: Artificial Sequence
<220> FEATURE:
<223> OTHER INFORMATION: Part of human EDG1
<220> FEATURE:
<221> NAME/KEY: misc_feature
<223> OTHER INFORMATION: Part of human EDG1

<400> SEQUENCE: 32
cagagcugcg gcuggccuug gaaaa                                                25

<210> SEQ ID NO 33
<211> LENGTH: 21
<212> TYPE: RNA
<213> ORGANISM: Artificial Sequence
<220> FEATURE:
<223> OTHER INFORMATION: Part of human EDG1
<220> FEATURE:
<221> NAME/KEY: misc_feature
<223> OTHER INFORMATION: Part of human EDG1

<400> SEQUENCE: 33
ccacggacag acgccgcugu g                                                   21

<210> SEQ ID NO 34
<211> LENGTH: 25
<212> TYPE: RNA
<213> ORGANISM: Artificial Sequence
<220> FEATURE:
<223> OTHER INFORMATION: Part of human EDG1
<220> FEATURE:
<221> NAME/KEY: misc_feature
<223> OTHER INFORMATION: Part of human EDG1

<400> SEQUENCE: 34
cacagcggcg ucuguccgug gaaaa                                                25

<210> SEQ ID NO 35
<211> LENGTH: 21
<212> TYPE: RNA
<213> ORGANISM: Artificial Sequence
<220> FEATURE:
<223> OTHER INFORMATION: Mutation
<220> FEATURE:
<221> NAME/KEY: misc_feature
<223> OTHER INFORMATION: Mutation

<400> SEQUENCE: 35
gaagcgaagu ugguggaucu g                                                   21

<210> SEQ ID NO 36
<211> LENGTH: 25
<212> TYPE: RNA
<213> ORGANISM: Artificial Sequence
<220> FEATURE:
<223> OTHER INFORMATION: Mutation
<220> FEATURE:
<221> NAME/KEY: misc_feature
<223> OTHER INFORMATION: Mutation

<400> SEQUENCE: 36
cagauccacc aacuucgcuu caaaa                                                25

<210> SEQ ID NO 37
<211> LENGTH: 21
<212> TYPE: RNA
<213> ORGANISM: Artificial Sequence
```

```
-continued

<220> FEATURE:
<223> OTHER INFORMATION: Mutation
<220> FEATURE:
<221> NAME/KEY: misc_feature
<223> OTHER INFORMATION: Mutation

<400> SEQUENCE: 37
gaagagaagu ugguggcucu g                                              21

<210> SEQ ID NO 38
<211> LENGTH: 25
<212> TYPE: RNA
<213> ORGANISM: Artificial Sequence
<220> FEATURE:
<223> OTHER INFORMATION: Mutation
<220> FEATURE:
<221> NAME/KEY: misc_feature
<223> OTHER INFORMATION: Mutation

<400> SEQUENCE: 38
cagagccacc aacuucucuu caaaa                                          25

<210> SEQ ID NO 39
<211> LENGTH: 21
<212> TYPE: RNA
<213> ORGANISM: Artificial Sequence
<220> FEATURE:
<223> OTHER INFORMATION: Mutation
<220> FEATURE:
<221> NAME/KEY: misc_feature
<223> OTHER INFORMATION: Mutation

<400> SEQUENCE: 39
cagauccaca accuucgcuu c                                              21

<210> SEQ ID NO 40
<211> LENGTH: 21
<212> TYPE: RNA
<213> ORGANISM: Artificial Sequence
<220> FEATURE:
<223> OTHER INFORMATION: Mutation
<220> FEATURE:
<221> NAME/KEY: misc_feature
<223> OTHER INFORMATION: Mutation

<400> SEQUENCE: 40
cagauccaca accuucgcuu c                                              21
```

SYNTHETIC DOUBLE-STRANDED OLIGONUCLEOTIDES FOR SPECIFIC INHIBITION OF GENE EXPRESSION

The present invention relates to novel oligonucleotide derivatives which are at least partly double-stranded and which have a 2'5'-linked oligonucleotide residue on at least one 3' end and to the use thereof for specific inhibition of gene expression.

The inhibition of gene expression with the aid of synthetic nucleic acids is becoming increasingly important. Typical representatives of these synthetic nucleic acids (oligonucleotides) are antisense oligonucleotides, ribozymes, DNA enzymes and external guide sequences (EGS). "Antisense oligonucleotides" are short single-stranded nucleic acid derivatives which bind via Watson-Crick base pairing to a complementary messenger ribonucleic acid (mRNA) whose translation into the corresponding protein is to be inhibited. In most cases antisense oligonucleotides exhibit their action according to a mechanism which is supported by cellular ribonuclease H (RNase H); numerous studies have shown evidence for this. RNase H which is present in all cells recognizes a double strand of DNA and RNA and cuts the mRNA complementary to said oligonucleotide via hydrolysis of one or in most cases more phosphodiester bonds. The way in which the oligonucleotides have to be modified in order for activation of RNase H to take place is known and is described, for example, in Uhlmann (2000) Curr. Opin. Drug Discov. Dev. 3, 203-213. Synthetic ribozymes carry this nuclease activity in their sequence. The most common type of ribozyme is the "hammerhead" ribozyme in which the consensus sequence GAAAC which is derived from naturally occurring ribozymes forms the RNase part and the flanking sequences form the antisense oligonucleotide part. DNA enzymes which, however, are not derived from naturally occurring ribozyme motifs but have been found by in-vitro selection, act in a similar way. EGS are synthetic RNA analogs which activate the cellular RNase P and bind via appropriate flanking sequences to the target mRNA and induce a specific mRNA degradation. All of the abovementioned oligonucleotide derivatives are employed such that the RNA-binding part is single-stranded and that interaction with the target mRNA inhibits the gene expression in a sequence-specific manner.

It is also possible for the gene expression to be inhibited by interaction with particular proteins with the aid of "decoy" oligomers which mimic the binding regions for transcription factors. Treatment with decoy agents makes it possible to intercept particular proteins, in particular transcription factors, in a sequence-specific manner and thereby prevent a transcription activation.

Finally, there are oligonucleotide derivatives which act at the DNA level. These include triplex-forming oligonucleotides (anti-gene oligonucleotides). "Anti-gene oligonucleotides" bind via Hoogsteen base pairing in the large groove of the DNA double helix with formation of a triple helix, thereby causing sequence-specific inhibition of the transcription of the genes. Another group of intracellularly acting oligonucleotide derivatives, the chimeraplasts, are used for specific gene correction.

A common problem of the inhibition of gene expression with the aid of synthetic oligonucleotides is that it is always necessary to assay a relatively large number of oligonucleotides against various regions of the target nucleic acid, in order to identify an efficient sequence. Furthermore, antisense oligonucleotides often inhibit gene expression only inefficiently or incompletely. Moreover, sequence-unspecific side effects were observed, which may be caused by the fact that even relatively short part sequences of about five bases in length activate RNase H. This is shown, for example, by "Woolf et al. (1992). Proc. Natl. Acad. Sci. U.S.A. 89, 7305-7309)". However, there are also side effects which are caused by interaction of the antisense oligonucleotides with proteins.

Recently, the use of double-stranded RNA for inhibiting gene expression has been described. Double-stranded RNA (dsRNA) is a signal for particular cells and organisms to induce a sequence-specific degradation of mRNA according to a process which is known as RNA interference (RNAi). The RNAi phenomenon was observed in a number of different organisms such as, for example, C. elegans, flies, fungi, plants and mouse embryos. RNAi is believed to be very similar or identical to post-transcriptional gene silencing (PTGS) found in plants. A simple injection of dsRNA of more than 500 base pairs (bp) in length, whose sense-strand sequence is identical to the target mRNA to be inhibited, can specifically inhibit expression of a target gene having the corresponding DNA sequence. This does not impair the expression of nonhomologous genes and the base sequence of the target gene is not altered. RNAi is a post-transcriptional process in which the dsRNA is first cleaved into relatively small fragments which are then probably used for sequence-specific degradation of the target mRNA. Apart from the double-strand nuclease activity, an ATP-dependent helicase activity is also discussed. However, the detailed mechanism of this process is not known. Studies in plants show that small dsRNA fragments of about 25 nucleotides in length represent the "active species" of the RNAi, which transfer the sequence-specific recognition of the target RNA to a cellular ribonuclease.

The efficiency of inhibiting gene expression with the aid of dsRNA decreases drastically with decreasing fragment length of said dsRNA. Thus it was found that dsRNA of from 400 to 540 bp inhibits the gene expression very effectively, while dsRNA of from 200 to 300 bp does so less efficiently and dsRNA of from 50 to 100 bp has no effect whatsoever. Only recently has it been found that small dsRNA fragments of from 26 to 81 bp in length are after all capable of causing an RNAi-like process. However, the observed inhibition appears to be substantially weaker than in the case of long dsRNA fragments. The inhibition produced by a 717 bp dsRNA was markedly more pronounced than that by a dsRNA of less than 200 bp in length. The 26 bp dsRNA was approx. 250 times less active than the 81 bp dsRNA. Moreover, the inhibition was sequence-dependent, since a different 27 bp dsRNA was not active at all.

Elbashir et al. Nature (2001) 411, 494 described an inhibition of gene expression in cell culture by a double-stranded RNA comprising 21 nucleotides. The corresponding dsRNA molecules contained on the 3' ends of both strands overhangs of 2 3'5'-linked nucleotides which have either uracil or thymine bases. The authors also note that 2'5'-oligoadenylate-activated ribonuclease processes lead to an intrinsic sequence-unspecific degradation of the target RNA. However, an obvious disadvantage is the fact that a successful inhibition strongly depends on the cell line used.

Previously, the gene expression was efficiently inhibited mainly by using dsRNA of more than 100 bp in length. This relatively long dsRNA is accessible only via in-vitro or in-vivo transcription from the corresponding DNA via suitable transcription systems. Another limitation of RNAi with long dsRNA is the fact that only particular organisms such as C. elegans, zebra fish, plants, particular types of fungi, Drosophila, oocytes and embryos of mice allow sequence-specific inhibition by dsRNA, while most animal cells when treated with dsRNA cause apoptosis. Long dsRNA still inhibits gene expression when the sequence homology is from 70 to 90%. For this reason, it is possible in the case of gene families with high sequence homology for misinterpretations of the phenotype to occur by simultaneous inhibition of the expression of a plurality of not completely homologous genes.

The treatment of cells with dsRNA, for example with dsRNA viruses, generally leads to an apoptotic process or to the sequence-unspecific degradation of the mRNA due to induction of a 2'5'-oligoadenylate-synthase activity. The infected cell synthesizes in response to the viral dsRNA trimeric or tetrameric adenylate (2'5'-A) with the unusual 2'5'-phosphodiester-internucleoside bond. 2'5'-A is phosphorylated by cellular kinases on its 5' end and then activates a nuclease called RNase L. 2'5'-A may also be chemically synthesized and be introduced into the cell (Torrence et al. (1994) Curr. Med. Chem 1, 176-191). However, synthetic 2'5'-A activates RNase L only if it has been converted to the 5'-phosphate or 5'-triphosphate form. RNase L activated by 5'-p-2'5'-A (p is phosphate, diphosphate or triphosphate) then degrades the entire RNA of the cell in a sequence-unspecific manner. In addition, it was shown that it is possible to inhibit gene expression sequence-specifically with the aid of antisense oligonucleotide conjugates with a 5'-p-2'5'-A residue. For this purpose, however, it is essential that the 5' end of the 2'5'-A residue is not linked to the oligonucleotide but is present as phosphate or triphosphate (Torrence et al. (1993) Proc. Natl. Acad. Sci. U.S.A. 90, 1300-4). Furthermore, the target RNA-recognizing oligonucleotide part (antisense part) must be in single-stranded form. For the reasons mentioned above, oligonucleotides having on their 3' ends 2'5'-A residues which consequently have no free 5'-phosphate or triphosphate function have not been described previously as inhibitors of gene expression. The inhibition of gene expression by the single-stranded, 5'-phosphorylated 5'-p-2'5'-A antisense oligonucleotide conjugates is a variation of the antisense principle and is therefore also subject to the limitations of the antisense-oligonucleotide approach.

Recently, oligonucleotides have been used increasingly as tools for studying the function of new genes (functional genomics). The use of antisense oligonucleotides and ribozymes for sequence-specific inhibition of gene expression of new genes coding for proteins with unknown function is made more difficult by the fact that generally a large variety of oligonucleotides of different sequences have to be assayed, and this is a disadvantage in particular for a high-throughput process.

It is therefore an object of the present invention to provide novel chemically modified oligonucleotides with significantly improved inhibition of gene expression, which circumvent the abovementioned limitations of the conventional methods and agents.

According to the invention, this object is achieved by novel oligonucleotide derivatives which are at least partly double-stranded and which have a 2'5'-linked oligonucleotide residue on at least one 3' end. The sequence of the novel oligonucleotide derivatives is complementary in one strand to the RNA sequence whose translation is to be inhibited and corresponds in the other strand to the RNA to be inhibited. The RNA double strand thus corresponds to the base sequence of the gene whose expression may be inhibited, with the deoxyribonucleotides being replaced by the corresponding ribonucleotides and thymidine being replaced by uridine.

The invention accordingly provides double-stranded nucleic acid derivatives of the formula I,

where

N and N' are naturally or not naturally occurring nucleotides which are at least partly complementary to one another and where at least one nucleotide strand $(N)_x$ or $(N')_y$ is complementary or partially complementary to a target gene or to the RNA corresponding thereto, x and y independently of one another are 10 to 100, preferably 15 to 45 and particularly preferably 16 to 25, n is 0 to 20, preferably 2 to 10, particularly preferably 3 to 6, m is 0 to 20, preferably 2 to 10, particularly preferably 3 to 6, p is 0 to 20, preferably 0 to 5, W and Z are naturally or not naturally occurring nucleotides which are linked via a 3'5' or 2'5' internucleoside bond, Li is a linker which covalently links the two nucleotide strands, wherein at least two residues Z or W are linked via a 2'5' internucleoside bond and are present in single-stranded form and m and n are not simultaneously zero.

Preference is given to oligonucleotides of the formula I whose homologous target RNA has the following sequence patterns:

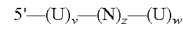

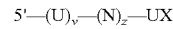

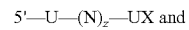

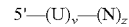

where v and w independently of one another are 2 to 20, preferably 2 to 10, particularly preferably 2 to 6 and z is 15 to 25, preferably 16 to 23 and particularly preferably 19 to 21 and U is uridine, N is A, G, C or U, and X is A, G or C, preferably A.

If the gene whose expression is to be inhibited contains, for example, the following DNA sequence

or the following RNA sequence

then the target RNA has the following sequence pattern 5'-$(U)_v$-$(N)_z$-UX, where v is 4, z is 19 and X is G.

Furthermore, preference is given to oligonucleotides of the formula I in which one or more phosphodiester bonds have been replaced, for example by phosphorothioate bonds or N3',P5'-phosphoramidate bonds. Particular preference is given to oligonucleotides of the formula I in which one or more phosphodiester bonds have been replaced by phosphorothioate residues. The phosphorothioate residues are preferably introduced on the 3' ends, the 5' ends and on the internal pyrimidine nucleotides C and U, in particular if several pyrimidine nucleotides succeed one another in the sequence. The phosphorothioate residues may be introduced in the upper or lower strand, preferably in both strands.

A particular embodiment of the invention comprises the use of a mixture of two or more oligonucleotide derivatives in accordance with formula 1 for inhibiting gene expression. The oligonucleotide derivatives in this case may be directed against different regions of an RNA or against the RNA of different genes.

Surprisingly, it was found that partially double-stranded nucleic acids which have a 2'5'-linked oligoadenylate residue on at least one end inhibit the gene expression much more strongly than double-stranded RNA comprising only 3'5'-linked nucleotides. The double-stranded RNA fragments having the 2'5'-linked oligoadenylate residue were also more active than the corresponding single strand having a 2'5'-linked oligoadenylate residue. This is surprising in that normally antisense oligonucleotides and sense oligonucleotides cancel out each other's action. Another surprise is that the 2'5'-linked oligoadenylate residue need not have a free end with a 5'-phosphate or 5'-triphosphate residue, in order to be able to exhibit its activity. It also came as a complete surprise that the 2'5'-linked oligoadenylate residue can be bound to the 3'5'-linked RNA directly via the 5' function. Surprisingly, a 2'5'-A residue in the coding strand had only a very small positive effect on the activity of the double strand as long as a 2'5'-A residue was present in the noncoding strand. Surprisingly, double-stranded RNA having on the lower strand overhanging ends of four to six bases is much more active than one having only two overhanging bases. In contrast to the antisense oligonucleotides of which generally a plurality of sequences (for example 10 to 100) have to be assayed in order to obtain an active sequence, surprisingly all of the assayed double-stranded oligonucleotides of the formula I were inhibition-active if they were homologous to the corresponding gene sequences. Surprisingly, no intrinsic unspecificity with the 2'5'-linked oligonucleotides was observed either. Previously, a 2'5'-active inhibition via double-stranded RNA had always been asscociated with an unspecific, i.e. sequence-independent, effect (Bass, Nature (2001) 411, 428).

A mixture of two 2'5'-(A)$_4$-oligonucleotides which do not form base pairs is less effective than the double-stranded molecules. Furthermore, compounds of the formula I are less effective or ineffective if their sequence is not perfectly homologous to the target RNA.

Surprisingly, the oligonucleotides of the invention also had an inhibitory sequence-specific effect on human primary cells. As far as we know, the inhibition of gene expression by double-stranded oligonucleotides in human primary cells has not been observed previously. It was likewise unexpected that for this only one strand of the double-stranded RNA had to have an overhanging end.

The inventive oligonucleotides of the formula I may also be used for inhibiting gene expression in cells which express only a small amount of, a defective or no 2'5'-oligoadenylate synthase. The described dsRNA molecules comprising 21 nucleotides (Elbashir et al. Nature (2001) 411, 494) do not have these properties.

It is furthermore also possible to use the oligonucleotides of the formula I for treating patients having a deficiency or defect in 2'5'-oligoadenylate synthase. Patients with CFS (chronic fatigue syndrome), for example, may also be treated. The sequences of the double-stranded nucleic acids which are used for inhibiting the gene expression of particular targets are selected on the basis of the corresponding gene sequences. The sequences of said genes are obtained by sequencing or from gene databases. An example which may be illustrated here is the inhibition of luciferase (firefly) by double-stranded nucleic acids. The accession number for this gene is U47298. The coding region of firefly luciferase comprises 1 653 nucleotides. The following four regions may be selected, inter alia, as target sequences for the inhibition by double-stranded nucleic acids.

```
        Gcttttacagatgcacatatcgaggtggacatcacttacg       (Seq ID No. 3)
  121   ---------+---------+---------+---------+  160
        cgaaaatgtctacgtgtatagctccacctgtagtgaatgc ccgcgaacgacatttataatgaacgtgaattgctcaacag       (Seq ID No. 4)
  311   ---------+---------+---------+---------+  350
        ggcgcttgctgtaaatattacttgcacttaacgagttgtc gcggtcggtaaagttgttccattttttgaagcgaaqgttg       (Seq ID No. 5)
 1081   ---------+---------+---------+---------+  1120
        cgccagccatttcaacaaggtaaaaaacttcgcttccaac attttttgaagcgaaggttgtggatctggataccgggaaa       (Seq ID No. 6)
 1101   ---------+---------+---------+---------+  1140
        taaaaaacttcgcttccaacacctagacctatggcccttt
```

The corresponding double-stranded RNA for these regions then has the following sequence.

```
        GCUUUUACAGAUGCACAUAUCGAGGUGGACAUCACUUACC       (Seq ID No. 7, 8)
  121   ---------+---------+---------+---------+  160
        CGAAAAUGUCUACGUGUAUAGCUCCACCUGUAGUGAAUGC

CCGCGAACGACAUUUAUAAUGAACGUGAAUUGCUCAACAG       (Seq ID No. 9, 10)
  311   ---------+---------+---------+---------+  350
        GGCGCUUGCUGUAAAUAUUACUUGCACUUAACGAGUUGUC

GCGGUCGGUAAAGUUGUUCCAUUUUUUGAAGCGAAGGUUG       (Seq ID No. 11, 12)
 1081   ---------+---------+---------+---------+  1120
        CGCCAGCCAUUUCAACAAGGUAAAAAACUUCGCUUCCAAC
```

```
            AUUUUUUGAAGCGAAGGUUGUGGAUCUGGAUACCGGGAAA         (Seq ID No. 13, 14)
       1101 ---------+---------+---------+---------+  1140
            UAAAAAACUUCGCUUCCAACACCUAGACCUAUGGCCCUUU
```

The inventive double-stranded nucleic acids derived therefrom have, for example, the sequences listed below and are characterized in that two or more nucleotides (indicated here by lower-case letters) in at least one strand are linked via a 2'5'-internucleoside bond. The overhanging ends may not be complementary to the target RNA. The number represents the region on the RNA, up means upper (coding) strand and lo means lower (noncoding) strand. Preference is given to 2'5'-linked adenylate residues. If in the formula I p equals zero, the two strands are held together only via hydrogen bonds.

```
     5'      UACAGAUGCACAUAUCGAGGUGaaaa    luc-126_up
     3'  aaaaAUGUCUACGUGUAUAGCUCCAC        luc-126_lo 5'      UAUAAUGAACGUGAAUUGCUCaaaa     luc-326_up
     3'  aaaaAUAUUACUUGCACUUAACGAG         luc-326_lo 5'      GGUAAAGUUGUUCCAUUUUUUaaaa     luc-1087_up
     3'  aaaaCCAUUUCAACAAGGUAAAAAA         luc-1087_lo 5'      GAAGCGAAGGUUGUGGAUCUGaaaa     luc-1108_up
     3'  aaaaCUUCGCUUCCAACACCUAGAC         luc-1108_lo
``` luc-126_up: Seq ID No. 15;
luc-126_lo: Seq ID No. 16;
luc-326_up: Seq ID No. 17;
luc-326_lo: Seq ID No. 18;
luc-1087_up: Seq ID No. 19;
luc-1087_lo: Seq ID No. 20;
luc-1108_up: Seq ID No. 21;
luc-1108_lo: Seq ID No. 22;

However, the oligonucleotides below, Seq ID Nos. 23 and 24, may also have, for example, 6 overhanging nucleotides in the lower strand, which are partially or completely 2'5'-linked.

```
     5'      GAAGCGAAGGUUGUGGAUCUG
     3'  aaaaAACUUCGCUUCCAACACCUAGAC

5'      GAAGCGAAGGUUGUGGAUCUG
     3'  aaaaaaCUUCGCUUCCAACACCUAGAC
```

An example of the structure of a strand of the double-stranded oligonucleotide is given below:

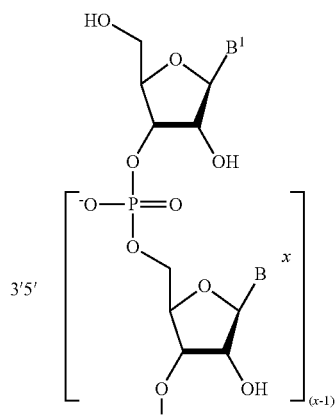

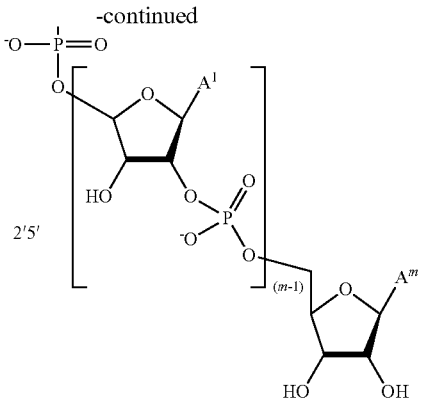

To test for biological activity, the following oligonucleotides, noted above as Seq ID Nos. 19, 20, 21 and 22, may be prepared, hybridized to a double strand, where appropriate, and tested for inhibition of luciferase activity in assay mixtures.

```
     3'  aaaaCCAUUUCAACAAGGUAAAAAA         luc-1087_lo

5'  GGUAAAGUUGUUCCAUUUUUUaaaa         luc-1087_up

5'      GGUAAAGUUGUUCCAUUUUUUaaaa     luc-1087_up
     3'  aaaaCCAUUUCAACAAGGUAAAAAA         luc-1087_lo 5'      GGUAAAGUUGUUCCAUUUUUU         luc-1087_up
     3'  aaaaCCAUUUCAACAAGGUAAAAAA         luc-1087_lo 3'  aaaaCUUCGCUUCCAACACCUAGAC         luc-1108_lo 5'  GAAGCGAAGGUUGUGGAUCUGaaaa         luc-1108_up 5'      GAAGCGAAGGUUGUGGAUCUGaaaa     luc-1108_up
     3'  aaaaCUUCGCUUCCAACACCUAGAC         luc-1108_lo 5'      GAAGCGAAGGUUGUGGAUCUG         luc-1108_up
     3'  aaaaCUUCGCUUCCAACACCUAGAC         luc-1108_lo 5'        CAAGCGAAGGUUGUGGAUCUGaaaa   luc-1108_up
     3'  aaaaaaCUUCGCUUCCAACACCUAGAC       luc-1108_lo 5'        GAAGCGAAGGUUGUGGAUCUG       luc-1108_up
     3'  aaaaaaCUUCGCUUCCAACACCUAGAC       luc-1108_lo 5'        GAAGCGAAGGUUGUGGAUCUGaaaa   luc-1108_up
     3'  teg-aaCUUCGCUUCCAACACCUAGAC       luc-1108_lo-teg 5'  GGUAAAGUUGUUCCAUUUUUUaaaa         luc-1087_up
     3'  aaaaCUUCGCUUCCAACACCUAGAC         luc-1108_lo 3'  aaaaCCAUUUCAACAAGCUAAAAAA         luc-1087_lo
     3'  aaaaCUUCGCUUCCAACACCUAGAC         luc-1108_lo
```

In order to show that the oligonucleotides of the invention may also be used for inhibiting gene expression in cells of other species, in particular in human primary cells, a compound of the invention may be directed, for example, against a human gene or the corresponding RNA thereof and assayed in human cells (HUVEC, human umbilical vein endothelial cells). For this, Edg-1 DNA (accession number M31210) from the gene database, for example, could be transcribed into the corresponding double-stranded RNA and the following two regions (175 and 725) could be selected for synthesizing appropriate oligonucleotides.

```
Edg-1 RNA:
"175"
      GACCUCGGUGGUGUUCAUUCUCAUCUGCUGCUUUAUCAUCCUGGAGAACAUCUUUGUCUU      (Seq ID No. 25, 26)
 141 ---------+---------+---------+---------+---------+---------+ 200
      CUGGAGCCACCACAAGUAAGAGUAGACGACGAAAUAGUAGGACCUCUUGUAGAAACAGAA

"725"
      AUUUCCAAGGCCAGCCGCAGCUCUGAGAAUGUGGCGCUGCUCAAGACCGUAAUUAUCGUC      (Seq ID No. 27, 28)
 721 ---------+---------+---------+---------+---------+---------+ 780
      UAAAGGUUCCGGUCGGCGUCGAGACUCUUACACCGCGACGAGUUCUGGCAUUAAUAGCAG
```

Examples of the possible structure of the corresponding oligonucleotides are disclosed below:

```
5'       AUCAUCCUGGAGAACAUCUUU         edg-1-175_up
3'-aaaaUAGUAGGACCUCIJUGUAGAAA          edg-1-175_lo 5'       CCAAGGCCAGCCGCAGCUCUG         edg-1-725_up
3'-aaaaGGUUCCGGUCGGCGUCCAGAC           edg-1-725_lo Mismatch control
5'       CCACGGACACACGCCGCUGUG         edg-1-mm_up
3'-aaaaGGUGCCUGUCUGCGGCGACAC           edg-1-mm_lo 5'       AUCAUCCUGGAGAACAUCUUU-FITC    edg-1-175_up_FITC
3'-aaaaUAGUAGGACCUCUUGUAGAAA           edg-1-175_lo
``` edg-1-175_up: Seq ID No. 29;
edg-1-175_lo: Seq ID No. 30;
edg-1-725_up: Seq ID No. 31;
edg-1-725_lo: Seq ID No. 32;
edg-1-mm_up: Seq ID No. 33;
edg-1-mm_up: Seq ID No. 34;

The number represents the region on the edg-1 RNA, up means upper (coding) strand and lo means lower (noncoding) strand. The mismatch control forms a perfectly paired double strand but differs from edg-1 RNA in 5 nucleotides (underlined as mismatch). FITC is a commercially available fluorescent marker.

Furthermore, the following oligonucleotides directed against edg-1 were prepared, which have improved nuclease stability and increased inhibitory activity and are derived from the above edg-1 sequences.

```
5'        A U*C A U*C*C*U G G A G A A*C A*U C*U*U*U-       (Seq ID No. 29)
FITC
5'        A U*C A U*C*C*U G G A G A A*C A*U C*U*U*U-teg    (Seq ID No. 29)
3'-a*a*a  a U*A G*U A G G A C*C*U C*U U G*U*A G A A*A      (Seq ID No. 30)
5'        C*C*A A G G*C*C A C*C*C C*C A G C*U*C*U*C*-      (Seq ID No. 31)
teg
3'-a*a*a  a G G U*U*C*C G G*U*C G G*C G*U*C G A G A*C      (Seq ID No. 32)
5'        C*C*A C*G G A C*A G A C*G C*C*G C*U*G*U*G-teg    (Seq ID No. 33)
3'-a*a*a  a G G U*G C*C*U G*U*C*U G*C G G*C G A*C A*C      (Seq ID No. 34)
```

Another embodiment of the present invention uses double-stranded oligonucleotides which have a 2'5'-linked overhanging residue only in one strand, preferably the noncoding strand, the two strands being held together via one or more covalent bonds. A possible example of this covalent bond is a linker of the $(Li)_p$ type.

edg-1-175_hairpin
```
5'       AUCAUCCUGGAGAACAUCUUU ┐ (Seq ID No. 29)
                          (Li)p
3'-aaaaUAGUAGGACCUCUUGUAGAAA ┘ (Seq ID No. 30)
```

For example, the two nucleic acid strands may be held together via a plurality of nucleotide residues, preferably four to five nucleotide residues (Li is N, preferably thymidine, p is 4 to 20, preferably 4 or 5).

```
5'       AUCAUCCUGGAGAACAUCUUU ┐     (Seq ID No. 29)
                                 (N)p
3'-aaaaUAGUAGGACCUCUUGUAGAAA ┘       (Seq ID No. 30)
```

In the case of the abasic linkers, the molecule has, for example, the following formula:

$$\begin{bmatrix} HO \\ \\ O \\ | \\ ^-O-P=O \\ | \\ O \end{bmatrix} \begin{bmatrix} B^1 \\ OH \end{bmatrix}_x \begin{bmatrix} B \\ OH \end{bmatrix}_{(x-1)}$$

-continued $$abasic \begin{bmatrix} ^-O-P=O \\ | \\ O \\ \\ H \\ H \\ O \\ | \end{bmatrix}_p$$

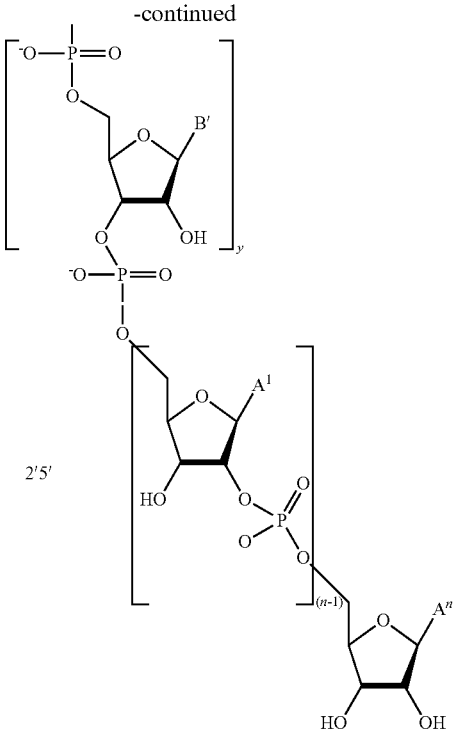

(abasic) from Glen Research, Sterling, Va.). The linker may also incorporate functional groups which, for example, increase the cellular uptake of the double-stranded oligonucleotide, increase the bioavailability, increase the nuclease stability or increase the biological activity. It is furthermore possible to incorporate groups for labeling, for example fluorescent markers or biotin markers, into the linker.

Other examples of linkers for linking the two strands are disulfide bridges (—S—S—) or pyrothiophosphate bridges (—(O₃)—P—S—S—P(O₃)—).

Alternatively, it is possible to hold the double strands together noncovalently via lipophilic or ionic interactions or via hydrogen bonds.

The specificity of the inhibition of luciferase expression was checked on the basis of double-stranded control oligonucleotides which are not completely homologous to the target RNA and have, for example, 2 or 4 base mismatches. Other control oligonucleotides vary with respect to the overhanging ends.

However, the two strands may also be held together via non-nucleotide residues. Examples of suitable non-nucleotide linkers are one or more oligoethylene glycol phosphate residues, preferably tri- and hexaethylene glycol phosphate residues. Examples of other linkers are alkanediol phosphates, preferably propane-1,3-diol phosphate, butane-1,4-diol phosphate and dodecyl-1,12-diol phosphate. Further examples of linkers are the abasic 1',2'-dideoxyribose units which are generally 3'-O, 5'-O-linked. The linker reagents required for the synthesis are mostly commercially available (e.g. Spacer 9, Spacer 18, Spacer C3, Spacer C12, dSpacer

```
5'        GAAGCGAAGGUUGUGGAUCUG       (Seq ID No. 23)
3' aaaaCUUCGCUUCCAACACCUAGAC          (Seq ID No. 22)

5'        GAAGCGAAGUUGGUGGAUCUG  2 mm (Seq ID No. 35)
3' aaaaCUUCGCUUCAACCACCUAGAC          (Seq ID No. 36)

5'        GAAGAGAAGUUGGUGGCUCUG  4 mm (Seq ID No. 37)
3' aaaaCUUCUCUUCAACCACCGAGAC          (Seq ID No. 38)

5'    GAAGCGAAGGUUGUGGAUCUG
3'    CUUCGCUUCCAACACCUAGAC            (Seq ID No. 39)

5'    GAAGCGAAGGUUGUGGAUCUGaaaa
3'    CUUCGCUUCCAACACCUAGAC            (Seq ID No. 40)
```

The following oligonucleotides described above as Seq ID Nos. 22 and 23, which have, for example, either phosphorothioate (asterisks) or 2'O-methylribonucleotide (underlined) modifications in the upper or lower strand or in both strands were prepared.

```
5'         G A A G C G A A G G U U G U G G A U C U G
3' a a a a-C*U*U*C G C*U*U C*C A A*C A C*C*U A G A*C

5'         G A A G C G A A G G U U G U G G A U C U G
3' a*a*a a-C*U*U*C G C*U*U C*C A A*C A C*C*U A G A*C

5'         G A A G C G A A G G U U G U G G A U C U G
3' a*U*U a-C*U*U*C G C*U*U C*C A A*C A C*C*U A G A*C

5'         G A A G C G A A G G U U G U G G A U C U G
3' a a a a-C U U C G C U U C C A A C A C C U A G A C

5'         G A A G C G A A G G U U G U G G A U C U G
3' a*a*a a-C*U*U*C G C*U*U C*C A A*C A C*C*U A G A*C

5'         G A A G C G A A G G U U G U G G A U C U G
3' a*U*U a-C*U*U*C G C*U*U C*C A A*C A C*C*U A G A*C

5'         G A A G*C G A A G G*U*U G*U G G A U*C*U*G-teg
3' a a a a-C U U C G C U U C C A A C A C C U A G A C 5'         G A A G C G A A G G U U G U G G A U C U G-teg
3' a a a a-C U U C G C U U C C A A C A C C U A G A C 5'         G A A G*C G A A G G*U*U G*U G G A U*C*U*G-teg
3' a a a a-C U U C G C U U C C A A C A C C U A G A C 5'         G A A G*C G A A G G*U*U G*U G G A U*C*U*G-teg
3' a*a*a a-C*U*U*C G C*U*U C*C A A*C A C*C*U A G A*C
```

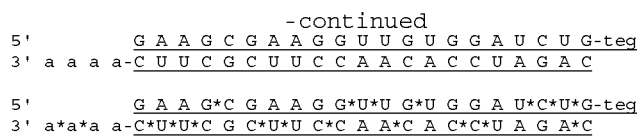

The inventive nucleic acid derivatives of formula I are synthesized from oligonucleotides. For example, an oligonucleotide may be synthesized completely from the nucleotides adenosine phosphate, guanosine phosphate, inosine phosphate, cytidine phosphate, uridine phosphate and thymidine phosphate. Preference is given to oligonucleotides which are synthesized from ribonucleotides, the "oligoribonucleotides". In other embodiments of the present invention, an oligonucleotide may contain, where appropriate, one or more modifications, for example chemical modifications. An oligonucleotide may have a plurality of identical and/or different modifications.

Examples of chemical modifications are known to the skilled worker and are described, for example, in E. Uhlmann and A. Peyman, Chemical Reviews 90 (1990) 543 and "Protocols for Oligonucleotides and Analogs" Synthesis and Properties & Synthesis and Analytical Techniques, S. Agrawal, Ed, Humana Press, Totowa, USA 1993, J. Hunziker and C. Leumann 'Nucleic Acid Analogs: Synthesis and Properties' in Modern Synthetic Methods (Ed. Beat Ernst and C. Leumann) Verlag Helvetica Chimica Acata, Basle, p. 331-417, RP Iyer et al. Curr Opin Mol Therap (1999) 1:344-358; S. Verma and F. Eckstein, Annu Rev Biochem (1998) 67:99-134; J W Engels and E. Uhlmann: Chemistry of oligonucleotides. In: *Pharmaceutical aspects of oligonucleotides*. Couvreur P, Malvy C (Eds), Taylor & Francis, London, (2000): 35-78.

The chemical modification of an oligonucleotide may include, for example, a) replacing completely or partially the phosphoric diester bridges with, for example, phosphorothioate, phosphorodithioate, $NR^1R^{1'}$phosphoramidate, boranophosphate, $(C_1$-$C_{21})$—O-alkyl phosphate, $[(C_6$-$C_{12})aryl$-$(C_1$-$C_{21})$—O-alkyl]$ phosphate, $(C_1$-$C_8)$alkyl phosphonate and/or $(C_6$-$C_{12})$ aryl phosphonate bridges, where $R^1$ and $R^{1'}$ independently of one another are hydrogen, $(C_1$-$C_{18})$alkyl, $(C_6$-$C_{20})$aryl, $(C_6$-$C_{14})$aryl-$(C_1$-$C_8)$alkyl, preferably hydrogen, $(C_1$-$C_8)$alkyl and/or methoxyethyl, particularly preferably hydrogen, $(C_1$-$C_4)$alkyl and/or methoxyethyl, or $R^1$ and $R^{1'}$, together with the nitrogen atom to which they are bound, form a 5-6-membered heterocycle which may additionally contain another heteroatom selected from the group consisting of O, S, N;

b) replacing completely or partially the 3'- and/or 5'-phosphoric diester bridges with "dephospho" bridges (described, for example, in Uhlmann, E. and Peyman, A. in "Methods in Molecular Biology", Vol. 20, "Protocols for Oligonucleotides and Analogs", S. Agrawal, Ed., Humana Press, Totowa 1993, Chapter 16, 355ff), for example with formacetal, 3'-thioformacetal, methylhydroxylamine, oxime, methylenedimethylhydrazo, dimethylenesulfone and/or silyl groups;

c) replacing partially the sugar phosphate backbone, for example with "morpholino" oligomers (described, for example, in E. P. Stirchak et al., Nucleic Acids Res. 17 (1989) 6129 and in J. Summerton and D. Weller, Antisense and Nucleic Acid Drug Dev. 7 (1997) 187-195) and/or with polyamide nucleic acids ("PNAs") (described, for example, in P. E. Nielsen et al, Bioconj. Chem. 5 (1994) 3) and/or phosphomonoester nucleic acids ("PHONAs") (described, for example, in Peyman et al., Angew. Chem. Int. Ed. Engl. 35 (1996) 2632-2638);

d) replacing partially the β-D-ribose units with, for example, β-D-2'-deoxyribose, α-D-2'-deoxyribose, L-2'-deoxyribose, 2'-F-2'-deoxyribose, 2'-F-2'-deoxyarabinofuranose, 2'-O—$(C_1$-$C_6)$alkylribose, 2'-O—$(C_2$-$C_6)$alkenylribose, 2'-[O—$(C_1$-$C_6)$alkyl-O—$(C_1$-$C_6)$alkyl]ribose, 2'-$NH_2$-2'-deoxyribose, β-D-xylofuranose, β-D-arabinofuranose, α-arabinofuranose, 2,4-dideoxy-β-D-erythrohexopyranose, conformationally restricted sugar analogs such as LNA (Locked nucleic acids; Singh et al., Chem. Commun. 4 (1998) 455; Singh et al. Chem. Commun. 12 (1998) 1247) and carbocyclic (described, for example, in Froehler, J. Am. Chem. Soc. 114 (1992) 8320) and/or open-chain sugar analogs (described, for example, in Vandendriessche et al., Tetrahedron 49 (1993) 7223) and/or bicyclo sugar analogs (described, for example, in M. Tarkov et al., Helv. Chim. Acta 76 (1993) 481). The 2'-modified oligonucleotide analogs are described in detail in Manoharan, Biochim. Biophys. Acta (1999) 117 and conformationally restricted oligonucleotide analogs in Herdewijn, Biochim. Biopyhs. Acta (1999) 167;

e) modifying and, respectively, completely or partially replacing the natural nucleoside bases with, for example, 5-(hydroxymethyl)uracil, 5-aminouracil, pseudouracil, pseudoisocytosine, dihydrouracil, 5-$(C_1$-$C_6)$alkyluracil, 5-$(C_2$-$C_6)$alkenyluracil, 5-$(C_2$-$C_6)$alkynylu racil, 5-$(C_1$-$C_6)$ alkylcytosi ne, 5-$(C_2$-$C_6)$alkenylcytosine, 5-$(C_2$-$C_6)$alkynylcytosine, 5-fluorouracil, 5-fluorocytosine, 5-chlorouracil, 5-chlorocytosine, 5-bromouracil, 5-bromocytosine or 7-deaza-7-substituted purines.

Heterocyclic base modifications are described, for example, in Herdewijn, Antisense & Nucl. Acid Drug Dev. (2000) 297.

The chemical modification of the oligonucleotide furthermore comprises conjugating an oligonucleotide with one or more molecules which influence advantageously the properties (e.g. nuclease stability, affinity for target sequence, pharmacokinetics) of said oligonucleotide and/or, during hybridization of the modified oligonucleotide to the target sequence, attack said target sequence with binding and/or crosslinking (oligonucleotide conjugates). Examples thereof are conjugates with polylysine, with intercalators such as pyrene, acridine, phenazine, phenanthridine, with fluorescent compounds such as fluorescein, with crosslinkers such as psoralen, azidoproflavin, with lipophilic molecules such as $(C_{12}$-$C_{20})$alkyl, with lipids such as 1,2-dihexadecyl-rac-glycerol, with steroids such as cholesterol or testosterone, with vitamins such as vitamin E, with poly- or oligoethylene glycol, with $(C_{12}$-$C_{18})$alkyl phosphate diesters and/or with —O—$CH_2$—CH(OH)—O—$(C_{12}$-$C_{18})$alkyl. Such molecules may be conjugated at the 5' and/or 3' end and/or within the sequence, for example at a nucleobase. Examples of oligonucleotide conjugates known to the skilled worker are described in Manoharan (2001) Conjugated Oligonucleotides in Antisense technology. In: Crooke (Editor) Antisense Technology. Marcel Dekker, New York.

A specific embodiment of the chemical modification relates to conjugation of the oligonucleotide a) with lipophilic molecules, for example $(C_{12}$-$C_{20})$alkyl, b) with steroids such as cholesterol and/or testosterone, c) with poly- and/or oligoethylene glycol, d) with vitamin E, e) with intercalators such as pyrene, f) with ($C_{14}$-$C_{18}$)alkyl phosphate diesters and/or g) with —O—$CH_2$—CH(OH)—O—($C_{12}$-$C_{16}$)alkyl.

Another specific embodiment of the chemical modification relates to derivatization of the oligonucleotide, as described in HMR 99/L045, as aryl ester conjugate, for example as FDA conjugate, which derivatization benefits the cellular uptake of said oligonucleotides.

Methods for preparing said oligonucleotide derivatives are known to the skilled worker and described, for example, in Uhlmann, E. & Peyman, A., Chem. Rev. 90 (1990) 543 and/or M. Manoharan in "Antisense Research and Applications", Crooke and Lebleu, Eds., CRC Press, Boca Raton, 1993, chapter 17, p. 303ff. and/or EP-A 0 552 766. The double strand may be prepared, for example, via hybridization of the two single strands by heating and then cooling solutions of said two single strands in diluted buffer. In principle, the methods described for gene synthesis can be used for preparing the double strand (Chemical and Enzymatic Synthesis of Gene Fragments (Editors: Gassen and Lang) Verlag Chemie, Weinheim (1982)).

In further specific embodiments of the present invention, the oligonucleotide, may have on its 3' and/or 5' end 3'-3' and/or 5'-5' inversions. This type of chemical modification is known to the skilled worker and described, for example, in M. Koga et al., J. Org. Chem. 56 (1991) 3757.

The 2'5'-overhanging residue may contain, for example, adenosine, 3'-deoxyadenosine (cordycepin), inosine, 8-bromoadenosine, 8-methyladenosine and other 8-substituted adenosine derivatives. The ribose residue may also be derivatized as 3'-O-methyladenosine. The internucleoside bonds in the 2'5'-overhanging part are preferably phosphodiester and phosphorothioate bonds. Common derivatives of 2'5'-adenylate, and the synthesis and RNase L activation thereof are described in the literature (Player et al. (1998) Pharmacol. Ther. 78, 55).

The invention further provides methods for preparing the oligonucleotides. The oligonucleotides described may be prepared with the aid of various known chemical methods, as described, for example, in Eckstein, F. (1991) "Oligonucleotides and Analogues, A Practical Approach", IRL Press, Oxford. The oligonucleotides may also be prepared by methods which, where appropriate, contain one or more enzymic steps.

The invention furthermore provides the use of the oligonucleotides for modulating and for completely or partially inhibiting the expression of particular target genes, for example for completely or partially inhibiting translation. The invention furthermore relates to the use of said oligonucleotides for modulating and for completely or partially inhibiting expression in cells which have only a small amount of, a defective or no 2'5'-oligoadenylate synthase.

The invention furthermore provides the use of said oligonucleotides as pharmaceuticals or to the use of said oligonucleotides for the production of pharmaceuticals. In particular, it is possible to use said oligonucleotides in pharmaceuticals which are suitable for the prevention and/or treatment of diseases which accompany the expression or overexpression of particular genes.

The invention further provides the use of said oligonucleotides or of pharmaceuticals containing said oligonucleotides for the treatment of diseases in which specific genes are the cause or are involved, due to overexpression.

The pharmaceuticals of the present invention may be used, for example, for the treatment of disorders caused by viruses, for example by CMV, HIV, HSV-1, HSV-2, hepatitis B, hepatitis C viruses, or papillomaviruses. Pharmaceuticals of the present invention are particularly suitable for the treatment of RNA viruses such as, for example, polio viruses, VSV or Influenza virus, in particular also of double-stranded RNA viruses such as reoviruses, for example.

The pharmaceuticals of the present invention are also suitable, for example, for cancer treatment. In this case it is possible, for example, to use oligonucleotide sequences which are directed against targets responsible for the development or growth of cancers. Examples of such targets are:
1) nuclear oncoproteins such as, for example, c-myc, N-myc, c-myb, c-fos, c-fos/jun, PCNA, p120,
2) cytoplasmic/membrane-associated oncoproteins such as, for example, EJ-ras, c-Ha-ras, N-ras, rrg, bcl-2, cdc-2, c-raf-1, c-mos, c-src, c-abl, c-ets,
3) cellular receptors such as, for example, EGF receptor, Her-2, c-erbA, VEGF receptor (KDR-1), retinoid receptors, protein kinase regulatory subunit, c-fms, Tie-2, c-raf-1 kinase, PKC-alpha, protein kinase A (R1 alpha),
4) cytokines, growth factors, extracellular matrix such as, for example, CSF-1, IL-6, IL-1a, IL-1b, IL-2, IL-4, IL-6, IL-8, bFGF, VEGF, myeloblastin, fibronectin,
5) inhibitors of tumor suppressor genes such as, for example, MDM-2.

The pharmaceuticals of the present invention are further suitable, for example, for the treatment of disorders which are influenced by integrins or cell-cell adhesion receptors, for example by VLA-4, VLA-2, ICAM, VCAM or ELAM.

The pharmaceuticals of the present invention are also suitable, for example, for preventing restenosis. In this connection, it is possible to use, for example, oligonucleotide sequences which are directed against targets responsible for proliferation or migration. Examples of such targets are:
1) nuclear transactivator proteins and cyclins such as, for example, c-myc, c-myb, c-fos, c-fos/jun, cyclins and cdc2 kinase,
2) mitogens or growth factors such as, for example, PDGF, bFGF, VEGF, EGF, HB-EGF and TGF-β,
3) cellular receptors such as, for example, bFGF receptor, EGF receptor and PDGF receptor.

The invention further relates to oligonucleotides for the treatment of asthma, with expression of the adenosine-A1 receptor, adenosine-A3 receptor, Bradikinin receptor or of IL-13 being inhibited with the aid of suitable oligonucleotides.

The invention also relates to oligonucleotides, for example, for the treatment of cardiovascular diseases, with, for example, expression of the β1-adrenergic receptor or of a protein from the EDG family such as, for example, Edg-1 being inhibited.

The invention also relates to oligonucleotides, for example, for the treatment of diabetes, with expression of PTP-1B being inhibited, for example.

The pharmaceuticals may be used, for example, in the form of pharmaceutical preparations which may be administered orally, for example in the form of tablets, coated tablets, hard or soft gelatin capsules, solutions, emulsions or suspensions. They may also be administered rectally, for example in the form of suppositories, or parenterally, for example in the form of injection solutions. Pharmaceutical preparations may be produced by processing said compounds in therapeutically inert organic and inorganic carriers. Examples of such carriers for tablets, coated tablets and hard gelatin capsules are lactose, corn starch or derivatives thereof, talc and stearic acid or salts thereof. Carriers suitable for the preparation of solutions are water, polyols, sucrose, invert sugar and glucose.

Carriers suitable for injection solutions are water, alcohols, polyols, glycerol and vegetable oils. Carriers suitable for suppositories are vegetable and hardened oils, waxes, fats and semisolid polyols. The pharmaceutical preparations may also contain preservatives, solvents, stabilizers, wetting agents, emulsifiers, sweeteners, colorants, flavorings, salts for modifying the osmotic pressure, buffers, coating agents, antioxidants and, where appropriate, other therapeutically active substances.

Preferred administration forms are topical administrations, local administrations such as, for example, with the aid of a catheter or by inhalation, injections or infusions, and oral administration. For injection, the oligonucleotide derivatives are formulated in a liquid solution, preferably in a physiologically acceptable buffer such as, for example, Hank's solution or Ringer's solution. However, the oligonucleotides may also be formulated in solid form and be dissolved or suspended prior to use. The dosages preferred for systematic administration are from approx. 0.01 mg/kg to approx. 50 mg/kg body weight and day.

The invention furthermore relates to pharmaceutical preparations which contain oligonucleotides and/or physiologically tolerated salts thereof in addition to pharmaceutically suitable carriers and/or additives.

The oligonucleotides and/or physiologically tolerated salts thereof may be administered to animals, preferably to mammals, and in particular to humans as pharmaceuticals on their own, in mixtures with one another or in the form of pharmaceutical preparations which permit topical, percutaneous, parenteral or enteral application and which contain as active ingredient an active dose of at least one oligonucleotide in addition to common pharmaceutically suitable carriers and additives. The preparations normally contain about from 0.1 to 90% by weight of the therapeutically active compound. For the treatment of skin disorders such as, for example, psoriasis or vitiligo, a topical application, for example in the form of ointments, lotions or tinctures, emulsions, or suspensions is preferred.

The pharmaceutical preparations are produced in a manner known per se (e.g. Remingtons Pharmaceutical Sciences, Mack Publ. Co., Easton, Pa.), with pharmaceutically inert inorganic and/or organic carriers being used. For the production of pills, tablets, coated tablets and hard gelatin capsules, lactose, corn starch and/or derivatives thereof, talc, stearic acid and/or salts thereof, etc. may be used, for example. Examples of carriers for soft gelatin capsules and/or suppositories are fats, waxes, semisolid and liquid polyols, natural and/or hardened oils, etc. Examples of carriers suitable for the preparation of solutions and/or syrups are water, sucrose, invert sugar, glucose, polyols, etc. Carriers suitable for the preparation of injection solutions are water, alcohols, glycerol, polyols, vegetable oils, etc. Carriers suitable for microcapsules, implants and/or rods are mixed polymers of glycolic acid and lactic acid. Liposome formulations which are known to the skilled worker (N. Weiner, Drug Develop Ind Pharm 15 (1989) 1523; "Liposome Dermatics, Springer Verlag 1992), for example HVJ liposomes (Hayashi, Gene Therapy 3 (1996) 878), are also suitable. Dermal administration may also be carried out, for example, with the aid of ionophoretic methods and/or with the aid of electroporation. In addition, it is possible to use lipofectins and other carrier systems, for example those which are used in gene therapy. Particularly suitable systems are those which can be used to introduce oligonucleotides into eukaryotic cells with great efficiency.

In addition to the active substances and the carriers, a pharmaceutical preparation may also contain additives such as, for example, fillers, extenders, disintegrants, binding agents, lubricants, wetting agents, stabilizers, emulsifiers, preservatives, sweeteners, colorants, flavorings or aromatizers, thickening agents, diluents, buffer substances, furthermore solvents and/or solubilizers and/or agents for achieving a depot effect, and also salts for modifying the osmotic pressure, coating agents and/or antioxidants. They may also contain two or more different oligonucleotides and/or their physiologically tolerated salts and furthermore, in addition to at least one oligonucleotide, one or more other therapeutically active substances.

The dose may vary within wide limits and, in each individual case, has to be adjusted to the individual circumstances.

EXAMPLES

1. Synthesis of the Oligonucleotides of the Formula 1 a) 3' aaaaaUGUCUACGUGUAUAGCUCCAC (Seq ID No. 16) (The bases indicated by lower-case letters have a 2'5'-internucleoside bond).

The syntheses were carried out in an ABI 394 DNA or Expedite synthesizer (Applied Biosystems, Weiterstadt, Germany). The synthesis cycles recommended by the manufacturer were used but for the ribonucleoside-2'-O-phosphoramidites the condensation step was doubled (with a coupling time of in each case 400 s) and the length of the iodine oxidation step was increased to 30 s. The solid phase used was a 1000 Å controlled pore glass (CPG) support which had 5'-O-dimethoxytrityl-N-6-benzoyladenosine (NSS-6101-10A, Chemgenes, Waltham, Mass.) bound via the 2' or 3' position of the sugar. After removing the 5'-O-dimethoxytrityl group by cleavage with trichloroacetic acid, the 2'5'-linked oligonucleotide part was synthesized by four condensations with 5'-O-dimethoxytrityl-N-6-benzoyl-3'-O-tertbutyldimethylsilyladenosine-2'-O-phosphoramidite (ANP-5681, Chemgenes). This was followed by synthesizing the 3'5'-linked oligonucleotide part by repeated condensation with the corresponding 5'-O-dimethoxytrityl-2'-O-tertbutyidimethylsilyinucleoside-3'-O-phosphoramidites (ANP-5671 to ANP-5680, Chemgenes). The CPG support was incubated with 750 μl of conc. ammonia/ethanol (3:1, v:v) with shaking at 30° C. for 24 hours in order to remove the oligomer from the support and to deprotect the phosphate and amino protective groups. The supernatant was separated from the support which was then washed twice more with 150 μl of conc. ammonia/ethanol (3:1, v:v). The combined supernatants were concentrated under reduced pressure and the residue was incubated with shaking in 1200 μl of triethylamine×3HF (very toxic) at 30° C. for 24 hours in order to remove the silyl protective groups. This is followed by adding 700 μl of n-butanol, cooling the mixture on dry ice for 30 minutes and centrifugation. The pellet was washed with butanol two more times. In addition, a sodium chloride precipitation was then carried out. 116 OD (260) of the crude product which shows only one main band in gelelectrophoresis were obtained. The product was further characterized by means of HPLC and electrospray mass spectrometry (negative mode) (calc. 8256.0, found 8256.8).

b) 3' aaaaAUAUUACUUGCACUUAACGAG (Seq ID No. 18)

The synthesis was carried out analogously to that of example 1a), with the 2'5'-linked oligonucleotide part being synthesized by three condensations with 5'-O-dimethoxytrityl-N-6-benzoyl-3'-O-tertbutyidimethylsilyladenosine-2'-O- phosphoramidite (ANP-5681, Chemgenes). 112 OD (260) of the crude product which shows only one main band in gelelectrophoresis were obtained. The product was further characterized by means of HPLC and electrospray mass spectrometry (negative mode) (calc. 7958.9, found 7958.6).

c) 3' aaaaCCAUUUCAACAAGGUAAAAAA (Seq ID No. 20)

The synthesis was carried out analogously to that of example 1b). 117 OD (260) of the crude product which shows only one main band in gelelectrophoresis were obtained. The product was further characterized by means of HPLC and electrospray mass spectrometry (negative mode) (calc. 8012.0, found 8011.8).

d) 3' aaaaCUUCGCUUCCAACACCUAGAC (Seq ID No. 22)

The synthesis was carried out analogously to that of example 1b). 117 OD (260) of the crude product which shows only one main band in gelelectrophoresis were obtained. The product was further characterized by means of HPLC and electrospray mass spectrometry (negative mode) (calc. 7868.8, found 7868.6).

e) 3' aaaaaaCUUCGCUUCCAACACCUAGAC (Seq ID No. 24)

The synthesis was carried out analogously to that of example 1a), with the 2'5'-linked oligonucleotide part being synthesized by five condensations with 5'-O-dimethoxytrityl-N-6-benzoyl-3'-O-tertbutyldimethylsilyladenosine-2'-O-phosphoramidite (ANP-5681, Chemgenes). 112 OD (260) of the crude product which shows only one main band in gelelectrophoresis were obtained. The product was further characterized by means of HPLC and electrospray mass spectrometry (negative mode) (calc. 8527.2, found 8527.5).

f) 3'teg-<u>AA</u>CUUCGCUUCCAACACCUAGAC (Seq ID No. 22) (where teg is a triethylene glycol phosphate residue)

The synthesis was carried out analogously to that of example 1a), using a triethylene glycol succinate-derivatized CGP support and preparing the 2'5'-linked oligonucleotide part according to the sequence by condensation with 5'-O-dimethoxytrityl-N-6-benzoyl-3'-O-tertbutyldimethylsilyladenosine-2'-O-phosphoramidite (ANP-5681, Chemgenes). 83 OD (260) of the crude product which contains a triethylene glycol phosphate residue on the 2' position of the 3'-terminal adenosine were obtained. The product was further characterized by means of HPLC and electrospray mass spectrometry (negative mode) (calc. 7422.5, found 7422.6).

g) 5'GAAGCGAAGGUUGUGGAUCUGaaaa (Seq ID No. 23)

The synthesis was carried out analogously to that of example 1b). 108 OD (260) of the crude product which shows only one main band in gelelectrophoresis were obtained. The product was further characterized by means of HPLC and electrospray mass spectrometry (negative mode) (calc. 8149.0, found 8148.9).

h) 5'-GGUAAAGUUGUUCCAUUUUUUaaaa (Seq ID No. 19)

The synthesis was carried out analogously to that of example 1b). 112 OD (260) of the crude product which shows only one main band in gelelectrophoresis were obtained. The product was further characterized by means of HPLC and electrospray mass spectrometry (negative mode) (calc. 7930.7, found 7930.7).

i) 5'-G A A G C G A A G G U U G U G G A U C U G (Seq ID No. 23)

The synthesis was carried out analogously to that of example 1a) but only 3'5'-internucleotide bonds were introduced. 82 OD (260) of the crude product which shows only one main band in gelelectrophoresis were obtained. The product was further characterized by means of HPLC and electrospray mass spectrometry (negative mode) (calc. 6832.2, found 6831.8).

j) 3' a a a a-C*U*U*C G C*U*U C*C A A*C A C*C*U A G A*C (Seq ID No. 22)

The synthesis was carried out analogously to that of example 1b). The phosphorothioate residue was introduced by using the Beaucage reagent (RN-1535, Chemgenes, Waltham, Mass.) rather than the iodine solution in the particular oxidation step. 112 OD (260) of the crude product which shows only one main band in gelelectrophoresis were obtained. The product was further characterized by means of HPLC and electrospray mass spectrometry (negative mode) (calc. 8029.4, found 8031.2).

k) 3' a*a*a a-C*U*U*C G C*U*U C*C A A*C A C*C*U A G A*C (Seq ID No. 22)

The synthesis was carried out analogously to that of example 1j). 128 OD (260) of the crude product which shows only one main band in gelelectrophoresis were obtained. The product was further characterized by means of HPLC and electrospray mass spectrometry (negative mode) (calc. 8061.6, found 8062.8).

l) 3' A*U*u a-C*U*U*C G C*U*U C*C A A*C A C*C*U A G A*C (Seq ID No. 22) (contains only one 2'5'-internucleotide bond between u a)

The synthesis was carried out analogously to that of example 1k). 96 OD (260) of the crude product which shows only one main band in gelelectrophoresis were obtained. The product was further characterized by means of HPLC and electrospray mass spectrometry (negative mode) (calc. 8015.5, found 8017.8).

m) 3' a a a a-C U U C G C U U C C A A C A C C U A G A C (Seq ID No. 22)(The bases indicated by lower-case letters have a 2'5'-internucleoside bond; the underlined nucleotides are 2'-O-methylribonucleotides)

The synthesis was carried out analogously to that of example 1a). In the case of the underlined nucleotides, 5'-O-dimethoxytrityl-2'-O-methyl-ribonucleoside-3'-O-phosphoramidites (ANP-5751 to ANP-5758, Chemgenes) were condensed. 99 OD (260) of the crude product which shows only one main band in gelelectrophoresis were obtained. The product was further characterized by means of HPLC and electrospray mass spectrometry (negative mode) (calc. 8163.4.6, found 8165.1).

n) 3' a*a*a a-C*U*U*C G C*U*U C*C A A*C A C*C*U A G A*C (Seq ID No. 22)

The synthesis was carried out analogously to that of example 1m). 127 OD (260) of the crude product which shows only one main band in gelelectrophoresis were obtained. The product was further characterized by means of HPLC and electrospray mass spectrometry (negative mode) (calc. 8356.1, found 8357.2).

o) 3'-aaaaUAGUAGGACCUCUUGUAGAAA (edg-1-175_lo) (Seq ID No. 30)

The synthesis was carried out analogously to that of example 1b). 134 OD (260) of the crude product which shows only one main band in gelelectrophoresis were obtained. The product was further characterized by means of HPLC and electrospray mass spectrometry (negative mode) (calc. 8037.9, found 8038.9).

p) 3'-aaaaGGUUCCGGUCGGCGUCGAGAC (edg-1-725_lo) (Seq ID No. 32)

The synthesis was carried out analogously to that of example 1b). 134 OD (260) of the crude product which shows only one main band in gelelectrophoresis were obtained. The product was further characterized by means of HPLC and electrospray mass spectrometry (negative mode) (calc. 8075.9, found 8076.9).

q) 3'-aaaaGGUGCCUGUCUGCGGCGACAC (edg-1-mm_lo) (Seq ID No. 34)

The synthesis was carried out analogously to that of example 1b). 109 OD (260) of the crude product which shows only one main band in gelelectrophoresis were obtained. The product was further characterized by means of HPLC and electrospray mass spectrometry (negative mode) (calc. 8035.9, found 8037.0).

r) 5' AUCAUCCUGGAGAACAUCUUU (edg-1-175_up) (Seq ID No. 29)

The synthesis was carried out analogously to that of example 1a) but only 3'5'-internucleotide bonds were introduced. The solid phase used was a 1000 Å controlled pore glass (CPG) support which held 5'-O-dimethoxytrityluridine (NSS-6104-10U, Chemgenes, Waltham, Mass.) bound via the 2' or 3' position of the sugar. 110 OD (260) of the crude product which shows only one main band in gelelectrophoresis were obtained. The product was further characterized by means of HPLC and electrospray mass spectrometry (negative mode) (calc. 6618.0, found 6618.5).

s) 5' AUCAUCCUGGAGAACAUCUUU-FITC (edg-1-175_up_FITC) (Seq ID No. 29)

The synthesis was carried out analogously to that of example 1a) but only 3'5'-internucleotide bonds were introduced. The solid phase used was a 500 Å controlled pore glass (CPG) support containing a protected fluorescein derivative (NSS-97505-A1CL, Chemgenes, Waltham, Mass.). 79 OD (260) of the crude product which shows only one main band in gelelectrophoresis were obtained. The product was further characterized by means of HPLC and electrospray mass spectrometry (negative mode) (calc. 7428.7, found 7432.3).

2. Inhibition of Luciferase Expression in SL-3 Cells

To test for biological activity, the following oligonucleotides, described above as Seq ID Nos. 19, 20, 21 and 22, were prepared, where appropriate hybridized to give the double strand and tested for inhibition of luciferase activity in the following assay mixtures.

|  |  |  | Assay mixture |
|---|---|---|---|
| 3' | aaaaCCAUUUCAACAAGGUAAAAAA | luc-1087_lo | 1 |
| 5' | GGUAAAGUUGUUCCAUUUUUUaaaa | luc-1087_up | 2 |
| 5' | GGUAAAGUUGUUCCAUUUUUUaaaa | luc-1087_up | 3 |
| 3' | aaaaCCAUUUCAACAAGGUAAAAAA | luc-1087_lo |  |
| 5' | GGUAAAGUUGUUCCAUUUUUU | luc-1087_up | 4 |
| 3' | aaaaCCAUUUCAACAAGGUAAAAAA | luc-1087_lo |  |
| 3' | aaaaCUUCGCUUCCAACACCUAGAC | luc-1108_lo | 5 |
| 5' | GAAGCGAAGGUUGUGGAUCUGaaaa | luc-1108_up | 6 |
| 5' | GAAGCGAAGGUUGUGGAUCUGaaaa | luc-1108_up | 7 |
| 3' | aaaaCUUCGCUUCCAACACCUAGAC | luc-1108_lo |  |
| 5' | GAAGCGAAGGUUGUGGAUCUG | luc-1108_up | 8 |
| 3' | aaaaCUUCGCUUCCAACACCUAGAC | luc-1108_lo |  |
| 5' | GAAGCGAAGGUUGUGGAUCUGaaaa | luc-1108_up | 9 |
| 3' | aaaaaaCUUCGCUUCCAACACCUAGAC | luc-1108_lo |  |
| 5' | GAAGCGAAGGUUGUGCAUCUG | luc-1108_up | 10 |
| 3' | aaaaaaCUUCGCUUCCAACACCUAGAC | luc-1108_lo |  |
| 5' | GAAGCGAAGGUUGUGGAUCUGaaaa | luc-1108_up | 11 |
| 3' | teg-aaCUUCGCUUCCAACACCUAGAC | luc-1108_lo-teg |  |
| 5' | GGUAAAGUUGUUCCAUUUUUUaaaa | luc-1087_up | 12 |
| 3' | aaaaCUUCGCUUCCAACACCUAGAC | luc-1108_lo |  |
| 3' | aaaaCCAUUUCAACAAGGUAAAAAA | luc-1087_lo | 13 |
| 3' | aaaaCUUCGCUUCCAACACCUAGAC | luc-1108_lo |  |

The assay mixtures 1, 2, 5, 6, 12 and 13 contain RNA which is not in double-stranded form. In contrast, the oligonucleotides in the assay mixtures 3, 4, 7, 8, 9, 10 and 11 are paired as double strands. The double strands 7, 9 and 11 have in both strands an overhanging 2'5'-linked oligonucleotide residue. The oligoribonucleotide luc-1108_lo contains on its 3' end only two overhanging 2'5'-linked nucleotides and a triethylene glycol phosphate residue (teg). The double strands of assay mixtures 8 and 10 have only one strand with a 2'5'-linked overhang.

Transfection: on the day before the experiment, $2 \times 10^6$ cells/ml were plated out into 6-well plates. The oligonucleotides were hybridized by heating the two strands in diluted buffer and subsequently cooling them to give the double strand and taken up in 100 μl of SF 90011 SFM (SF-900 serum-free insect medium II; Gibco BRL 10902-096). For transfection, 10 μl of lipofectin (1 mg/ml; Gibco BRL) were mixed with 100 μl of SF 90011 SFM and incubated at room temperature for 15 min. This was followed by pipetting together the lipofectin mix and the nucleic acid and incubating at room temperature for 15-45 min. In the meantime, the cells were washed with 3 ml of serum-free medium and 800 µl of SF 90011 SFM and the nucleic acid/lipofectin mixture were successively added to the cells, followed by incubation at 25 degrees overnight. On the next day, 1 ml of medium and+serum (Gibco BRL 10122-166; final concentration 2%) is added.

Dual-luciferase reporter (DLR; Promega E1960) assay system: (http://www.promega.com/catalog/CatalogProducts.asp?catalog%5Fname=Promega%5FProducts&category%5Fname=Dual%2DLuciferase+Reporter+Assay+System&description%5Ftext=Dual%2DLuciferase%3Csup%3E%26reg%3B%3 C%2Fsup%3E+Reporter+Assay+System)

The Promega DLR assay allows the sequential determination of the firefly luciferase and Renilla luciferase activities having different nucleic acid sequences from a single sample. The oligonucleotides according to the formula I, which were to be measured, were directed against firefly luciferase. Thus, only firefly luciferase activity but not Renilla luciferase activity should be inhibited. Thus, apart from the inhibitory action, the specificity may also be tested for.

The passive lysis of the cells in the well plates was carried out by first removing the medium and washing the cells with PBS (phosphate-buffered saline (Gibco BRL 14200-067). The medium was completely removed by suction and then the PLB (passive lysis buffer, diluted 1:5 with water; 500 µl of PLB (1×) to be introduced into one well of a 6-well plate) was added thereto. This was followed by a 15-minute incubation with shaking at room temperature.

The luciferase assay reagent II (LAR II) was prepared by resuspending the luciferase assay substrate (LAS) in 10 ml of luciferase assay buffer II (LAB II). The Stop & Glo reagent was prepared by adding 200 µl of the Stop & Glo substrate (solution) into the bottle containing dry Stop & Glo substrate and mixing the solution for 10 seconds using a vortexer. In order to produce a 1× Stop & Glo solution, 20 µl of the 50× Stop & Glo substrate and 1 ml of the Stop & Glo buffer are combined. This is sufficient for 10 assays.

DLR-assay: 100 µl of LAR II were introduced together with 20 µl of cell lysate into a well and mixed by pipetting up and down for 2-3 seconds. After luminometric measurement of firefly luciferase activity, 100 µl of Stop & Glo reagent were added, the solution was mixed and then the Renilla-luciferase activity was determined. The luminescence was determined using the Fluoroskan Ascent FL luminometer (Thermo Labsystems, Frankfurt, Germany).

| Assay mixture | Type | % Inhibition of firefly luciferase |
|---|---|---|
| 1 | ss | 13 |
| 2 | ss | 12 |
| 3 | ds | 44 |
| 4 | ds | 53 |
| 5 | ss | 19 |
| 6 | ss | 17 |
| 7 | ds | 56 |
| 8 | ds | 57 |
| 9 | ds | 42 |
| 10 | ds | 51 |
| 11 | ds | 20 |
| 12 | ss | 7 |
| 13 | ss | 18 | ss is single strand, ds is double strand

The double-stranded oligonucleotides (3,4, 7-10) inhibited firefly-luciferase activity to a substantially greater extent than the corresponding single-stranded molecules (1,2, 5,6, 12 and 13), with the exception of the double strand with only 2 overhanging nucleotides in the lower strand (assay mixture 11). An overhanging 2'5'-(A)$_4$ residue in the upper strand had no effect or only a very small positive effect on the activity of the double strand, as long as there was a 2'5'-(A)$_4$ residue in the lower strand (cf. 3 vs. 4 and 7 vs. 8). A 2'5'-(A)$_4$ residue in the lower strand caused a markedly improved action of the double strand compared with a 2'5'-(A)$_2$ residue (cf. 7 and 8 vs. 11). 5). A mixture of two single-stranded 2'5'-(A)$_4$ oligonucleotides, which were unable to form a double strand due to noncomplementary bases (12 and 13), was much less effective than double strands with complementary bases and overhanging 2'5'-adenylate residues.

Likewise, the following modified oligonucleotides of the formula I, described above as Seq ID Nos. 21 and 22, were assayed in the assay mixtures 14 to 18.

```
                                                                    Assay
                                                                    mixture 5'         G A A G C G A A G G U U G U G G A U C U G                14
3' a*a*a a-C*U*U*C G C*U*U C*C A A*C A C*C*U A G A*C 5'         G A A G C G A A G G U U G U G G A U C U G                15
3' a a a a-C U U C G C U U C C A A C A C C U A G A C 5'         G A A G*C G A A G G*U*U G*U G G A U*C*U*G-                16
teg
3' a*a*a a-C*U*U*C G C*U*U C*C A A*C A C*C*U A C A*C 5'                                                                   17
G A A G*C G A A G G*U*U G*U G G A U*C*U*G-teg
3' a*a*a a-C*U*U*C G C*U*U C*C A A*C A C*C*U A G A*C 5'                                                                   18
G A A G*C G A A G G*U*U G*U G G A U*C*U*G-teg
```

*is phosphorothioate, N: 2'-O-methyl-RNA, aaaa: 2'5'-linked adenylate

| Assay mixture | Type | % Inhibition of firefly luciferase |
|---|---|---|
| 14 | ds | 67 |
| 15 | ds | 2 |
| 16 | ds | 93 |
| 17 | ds | 0 |
| 18 | ss | 0 |
| 1100 bp dsRNA | | 94 |
| without dsRNA | | 0 | ss is single strand, ds is double strand

The introduction of phosphorothioate residues at particular positions in the lower strand (assay mixture 14) or in the lower and upper strands (assay mixture 16) led to a markedly improved action of the oligonucleotides of the invention, while introduction of 2'-O-methyl radicals in the entire lower or upper strand (assay mixtures 15 and 17) led to a strong decrease in activity. Surprisingly, the small oligonucleotide of assay mixture 16 inhibited the expression of firefly luciferase just as well as the very long (approx. 1100 bp) double-stranded RNA. The single strand (assay mixture 18) was likewise ineffective.

3. Inhibition of edg-1Expression in Human Primary Umbilical Cells (HUVEC).

In order to show that the oligonucleotides of the invention can also be used for inhibiting gene expression in human primary cells, said oligonucleotides were also directed against a human gene or the corresponding RNA and tested on human cells (HUVEC, human umbilical vein endothelial cells). The appropriate oligonucleotides were synthesized.

```
                                                                    Assay
                                                                   mixture 5'      AUCAUCCUGGAGAACAUCUUU     edg-1-175_up    (Seq ID No. 29)     14
3'-aaaaUACUAGGACCUCUUGUAGAAA      edg-1-175_lo    (Seq ID No. 30)

5'      CCAAGGCCAGCCGCAGCUCUG     edg-1-725_up    (Seq ID No. 31)     15
3'-aaaaGGUUCCGGUCGGCGUCGAGAC      edg-1-725_lo    (Seq ID No. 32)

Mismatch control
5'      CCACGGACAGACGCCGCUGUG     edg-1-mm_up     (Seq ID No. 33)     16
3'-aaaaGGUGCCUGUCUGCGGCGACAC      edg-1-mm_up     (Seq ID No. 34)

5'      AUCAUCCUGGAGAACAUCUUU-    edg-1-175_up_FITC  (Seq ID No. 29)  17
FITC
3'-aaaaUAGUAGGACCUCUUGUAGAAA      edg-1-175_lo    (Seq ID No. 30)
```

The double-stranded oligonucleotides of assay mixtures 14 to 16 contain only in one strand (noncoding) a 2'5'-linked overhanging residue. This feature is also a particular embodiment of the present invention.

Cells (HUVECs) and detection of cellular uptake. Transfection: 24 h prior to the actual transfection, primary HUVECs (2nd passage, isolated according to Jaffe et al., 1973, J. Clin.Invest 52, pp. 2745), were plated out at a density of $2.5\times10^5$ cells/well in 6-well plates coated with collagen-I from rats (Biocoat, #354400, Becton Dickinson). Equimolar amounts of strand and counterstrand of the particular oligonucleotides (in each case 1 mM in sterile-filtered PBS, pH 7.4, Gibco BRL #14200-067) were mixed and hybridized by incubating at 95° C. for five minutes, subsequent cooling to room temperature and incubating at 4° C. for five minutes. For transfection, 6 µl of lipofectin (1 mg/ml; Gibco BRL, #18292-011) were mixed with 200 µl of serum-free Opti-MEM 1 medium (Gibco BRL, 31985-047) and incubated at room temperature for 15 minutes. In a parallel reaction, a solution of 10 µM (→final concentration 0.1 µm) or 100 µm (→final concentration 1 µm) hybridized oligonucleotide (in PBS, pH 7.4) was diluted in a ratio of 1:10 with serum-free Opti-MEM 1 medium and mixed with the same volume of preincubated lipofectin solution. After incubation at room temperature for 15 minutes, the volume of said mixture was increased to 2 ml with serum-free Opti-MEM 1 medium and the cell lawn was washed once with PBS and then incubated with said mixture at 37° C., 5% $CO_2$ and 95% humidity for 4 hours. Subsequently, the cell lawn was washed again with PBS and then overlaid with serum-containing EGM medium (CellSystems, #CC-3024+EGM supplements #CC-3124) and incubated for a further 24 or 48 h. In the case of uptake studies using fluorescently labeled oligonucleotides, the cells were incubated for 4 hours, then fixed with 5% paraformaldehyde (in PBS, pH 7.4) and directly photographed in an inverted fluorescence microscope (Zeiss Axiovert 135M) with its 200-fold magnification using a cooled CCD camera (ORCA-1, Bfi optilas) and excitation through an FITC filter (excitation: 490 nm, emission: 510 nm) and processed via AQM2000 software (Kinetic Imaging).

Western blot analysis: the cells were lysed by washing the cell lawn once with PBS and then overlaying it with 200 µl/well 233 Laemmli buffer (Bio-Rad #161-0737). After incubation at room temperature for five minutes, the cell lysate was collected using a cell scraper (Becton Dickinson, #3085) and, prior to discontinuous 12% SDS polyacrylamide gel electrophoresis (SDS-PAGE, Laemmli et al., 1970, Bio-Rad-Criterion-System #345-0014), heated at 95° C. for 5 minutes and 45 µl of this solution were applied to each slot. The gel was run in 1×Tris/glycine/SDS buffer (Bio-Rad #161-0732). For the immunoblot, the gel was transferred with the aid of the Bio-Rad criterion Western blot apparatus (#170-4070) to a nitrocellulose (NC) membrane (Amersham #RPN 2020D) in 1×Tris/glycine buffer (Bio-Rad #161-0732, +10% methanol). The NC membrane was then saturated at room temperature for 1 hour using 1×TBS buffer (Bio-Rad #170-6435), which contained 5% milk powder ("Blotto", Bio-Rad #170-6404) and 0.1% Tween 20 (Bio-Rad #170-6531). After washing the membrane three times in Blotto-free TBS-Tween (TBST) buffer, the membrane was incubated with the anti-hEDG-1 primary antibody (polyclonal rabbit serum obtained by immunization with the EDG-1-specific peptide sequence CKAHRSSVSDYVNYD, coupled to KLH and affinity-purified against the abovementioned peptide sequence) in a 1:50 dilution in TBST-Blotto at 4° C. overnight. After washing three times with TBST, the secondary antibody (anti-rabbit, alkaline phosphatase-coupled, Dianova #111-055-045) was incubated in a 1:2000 dilution in TBST-Blotto at room temperature for one hour. After another washing step (see above), the ECF ("enhanced chemifluorescence") detection reaction (Amersham #RPN5785) was carried out, and the NC membrane which was covered with clingfilm was incubated with 1 ml of ECF substrate (Amersham Pharmacia #RPN5785) at room temperature for 5 minutes and then detected using a Fluor-Imager 595 scanner (Amersham Pharmacia). The signal was quantified using the ImageQuant software (Amersham Pharmacia) and normalized to the β-tubulin signal which was obtained after destaining (Alpha Diagnostic Kit #90100) the NC membrane once and incubating the β-tubulin-specific primary antibody (affinity-purified rabbit antibody, Santa Cruz #sc-9104) according to the above-described method.

| Concentration of ds RNA (μM) | EDG-1 Protein (% of control) | | |
|---|---|---|---|
| | Assay mixture 14 (Region "175") | Assay mixture 15 (Region "725") | Assay mixture 16 (mismatch) |
| 0.0 | 100 | 100 | 100 |
| 0.1 | 51 | 121 | 119 |
| 1.0 | 23 | 51 | 118 |

Treatment of the primary HUVEC cells with the double-stranded oligonucleotides of the invention led to a dose-dependent inhibition of Edg-1 expression. The inhibition proved to be target gene-specific, since, after treatment with the edg-1-specific oligonucleotides, only the edg-1 protein levels and not the tubulin levels were reduced in assay mixtures 14 and 15. The inhibition also proved to be sequence-specific with regard to the oligonucleotides used, since only the edg-1-homologous oligonucleotides of assay mixtures 14 and 15 inhibited edg-1 expression, while the double-stranded nucleic acid of assay mixture 16 which differs from the edg-1 sequence in 5 nucleotides did not inhibit edg-1 expression.

We believe that this is the first experiment to describe sequence-specific inhibition of gene expression in human primary cells by double-stranded RNA.

The cellular uptake in HUVEC cells was checked with the aid of the fluorescently labeled double-stranded oligonucleotide of assay mixture 17. After incubating the assay mixture 17 for 4 hours, good cellular uptake was detected with the aid of fluorescence microscopy. The double-stranded oligonucleotide taken up was mainly located in the cytoplasm, whereas a single-stranded FITC-labeled oligonucleotide was mainly found in the nucleus under the same conditions.

4. Inhibition of edg-1 Expression in Human Primary Umbilical Cells (HUVEC) with the Aid of Phosphorothioate-modified Oligomers The oligoribonucleotide analogues which had been modified with phosphoro-thioate at particular positions were used, as described in example 3, in primary human cells in order to inhibit gene expression of Edg-1 in human cells (HUVEC, human umbilical vein endothelial cells).

```
Assay mixture 18:
5'          A U*C A U*C*C*U G G A G A A*C A*U C*U*U*U-teg  (Seq ID No. 29)
3'-a*a*a a U*A G*U A G G A C*C*U C*U*U G*U*A G A A*A      (Seq ID No. 30)
Assay mixture 19:
5'          C*C*A A G G*C*C A G*C*C G*C A G C*U*C*U*G-teg (Seq ID No. 31)
3'-a*a*a a G G U*U*C*C G G*U*C G G*C G*U*C G A G A*C      (Seq ID No. 32)
Assay mixture 20:
mismatch:
5'          C*C*A C*G G A C*A G A C*G C*C*G C*U*G*U*G-    (Seq ID No. 33)
teg
3'-a*a*a a G G U*G C*C*U G*U*C*U G*C G G*C G A*C A*C      (Seq ID No. 34)
``` where * is phosphorothioate; (a*a*a a) is a 2'5'-linked adenylate (partially modified with *) and teg is a triethylene glycol phosphate.

The double-stranded oligoribonucleotides of assay mixtures 18 to 20 contain only in one strand (noncoding) a 2'5'-linked overhanging residue, with only particular internucleotide bonds being modified with phosphorothioate. This feature is likewise a particular embodiment of the present invention.

| Concentration of ds RNA (μM) | EDG-1 protein (% of control) | | |
|---|---|---|---|
| | Assay mixture 18 (region "175") | Assay mixture 19 (region "725") | Assay mixture 20 (mismatch) |
| 0.0 | 100 | 10 | 100 |
| 0.1 | 46 | 37 | 112 |
| 1.0 | 27 | 27 | 109 |

This experiment was repeated using a greater variation in the dosage.

| Concentration of ds RNA (μM) | EDG-1 protein (% of control) | | |
|---|---|---|---|
| | Assay mixture 18 (region "175") | Assay mixture 19 (region "725") | Assay mixture 20 (mismatch) |
| 0 | 100.0 | 100.0 | 100.0 |
| 0.01 | 107.7 | 95.6 | 93.4 |
| 0.05 | 71.9 | 93.4 | 115.7 |
| 0.1 | 49.9 | 61.7 | 100.8 |
| 0.5 | 43.5 | 25.8 | 125.0 |
| 1.0 | 25.1 | 12.8 | 113.5 |

The treatment of the primary HUVEC cells with the chemically modified double-stranded oligoribonucleotides of the invention led to a dose-dependent inhibition of edg-1 expression. Said inhibition proved to be target gene-specific, since, after treatment with the edg-1-specific oligonucleotides, only the Edg-1 protein levels but not the tubulin levels were reduced in assay mixtures 18 and 19. The inhibition also proved to be sequence-specific with regard to the oligo-nucleotides used, since only the edg-1-homologous oligonucleotides of assay mixtures 18 and 19 inhibited edg-1 expression, while the double-stranded nucleic acid of assay mixture 20 which differs from the edg-1 sequence in 5 nucleotides did not inhibit edg-1 expression.

The invention claimed is:

1. A double-stranded RNA oligonucleotide of Formula I

5'-(U)vX-(N)x-(W)-3'

3'-(Z)n-(N')y-5'    Formula I wherein

N and N' are naturally occurring nucleotides bound by 3',5' internucleotide bonds, wherein a portion of the oligonucleotide is double-stranded between (N)x and (N')y, and wherein the nucleotide strand (N)x, is sufficiently complementary to a target RNA to hybridize thereto and inhibit its expression through RNA interference, and wherein the nucleotide strand (N')y is at least partially homologous to the target RNA, and wherein N is selected from the group consisting of adenine (A), cytosine (C), guanine (G), and uracil (U);

x is independently 15-25;

y is independently 15-25;

n is independently 4 to 6;

v is independently 1 to 20, whereas: when v=1, X is selected from the group consisting of A, C, and G, and when v=2 to 20, X is absent;

W is selected from the group consisting of U2-20, UA, UC, and UG, or is absent; and Z is A; nucleotides of W being linked via a 3',5' internucleotide bond, and wherein at least two nucleotides of Z are linked via a 2',5' internucleotide bond and are present in a single-stranded form that does not base pair with the target gene or with the RNA homologous thereto, thereby forming a 2',5' linked oligonucleotide residue on the 3' end of the nucleotide strand (N')y and wherein the internucleotide bonds in the double-stranded oligonucleotide are 3',5' or 2',5' internucleotide bonds.

2. The double-stranded RNA of claim 1, wherein v is 2 to 10.

3. The double-stranded RNA of claim 2, wherein v is 2 to 6.

4. The double-stranded RNA of claim 1, wherein $U_{2-20}$ is $U_{2-10}$.

5. The double-stranded RNA of claim 4, wherein $U_{2-20}$ is $U_{2-6}$.

6. The double-stranded RNA of claim 1, wherein x is 16 to 23.

7. The double-stranded RNA of claim 6, wherein x is 19 to 21.

8. The double-stranded RNA of claim 1, wherein Z is adenosine or 3'-deoxyadenosine.

9. The double-stranded RNA of claim 1, in which one or more natural phosphodiester bonds have been replaced by unnatural internucleotide bonds that stabilize against nuclease degradation.

10. The double-stranded RNA of claim 9, in which one or more natural phosphodiester bonds have been replaced by phosphorothioate bonds.

11. The double-stranded RNA of claim 10, in which a plurality of natural phosphodiester bonds have been replaced by phosphorothioate bonds, with said replacements being located on the 5' or 3' ends of the oligonucleotide, and on internal pyrimidine nucleotides of the oligonucleotide.

12. The double-stranded RNA of claim 1, wherein one of nucleotide strands $(N)_x$ or $(N')_y$, is between 23 and 65 nucleotides in length and the other of the nucleotide strands is between 23 and 31 nucleotides in length.

13. The double stranded RNA of claim 1, wherein the double stranded RNA comprises one or more 2' O-methylribonucleotides.

14. The double stranded RNA of claim 1, wherein the double stranded RNA comprises one or more 2' fluoro-2'-deoxyribonucleotides.

15. The double stranded RNA of claim 1, wherein the double stranded RNA comprises one or more locked nucleic acids (LNA).

16. The double stranded RNA of claim 1, wherein the double stranded RNA further comprises a linker that links the two RNA strands.

17. The double stranded RNA of claim 16, wherein the linker is a nucleotide linker.

18. The double stranded RNA of claim 16, wherein the nucleotide linker comprises thymidine.

19. The double stranded RNA of claim 16, wherein the nucleotide linker comprises 4-20 nucleotide residues.

20. The double stranded RNA of claim 19, wherein the 4-20 nucleotide residues comprise one or more thymidines.

21. The double stranded RNA of claim 19, wherein the 4-20 nucleotide residues are thymidines.

22. The double stranded RNA of claim 16, wherein the nucleotide linker comprises 4-5 nucleotide residues.

23. The double stranded RNA of claim 22, wherein the 4-5 nucleotide residues comprise one or more thymidines.

24. The double stranded RNA of claim 23, wherein the 4-5 nucleotide residues are thymidines.

25. The double stranded RNA of claim 16, wherein the linker is a non-nucleotide linker.

* * * * *